US008395775B2

(12) United States Patent
Okawa

(10) Patent No.: US 8,395,775 B2
(45) Date of Patent: Mar. 12, 2013

(54) FLUORESCENT AGENT CONCENTRATION MEASURING APPARATUS, DOSE CONTROL APPARATUS, ADMINISTRATION SYSTEM, FLUORESCENT AGENT CONCENTRATION MEASURING METHOD, AND DOSE CONTROL METHOD

(75) Inventor: Atsushi Okawa, Hachioji (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 13/105,515

(22) Filed: May 11, 2011

(65) Prior Publication Data

US 2011/0213562 A1    Sep. 1, 2011

Related U.S. Application Data

(63) Continuation of application No. 11/327,866, filed on Jan. 9, 2006, now Pat. No. 7,966,051.

(30) Foreign Application Priority Data

Jan. 11, 2005 (JP) ................................. 2005-004577
Oct. 4, 2005 (JP) ................................. 2005-291599
Dec. 22, 2005 (JP) ................................. 2005-370668

(51) Int. Cl.
*G01N 21/00* (2006.01)
(52) U.S. Cl. ........................................ 356/432; 356/436
(58) Field of Classification Search ........... 356/432–436
See application file for complete search history.

(56) References Cited

U.S. PATENT DOCUMENTS

| 4,556,057 A | 12/1985 | Hiruma et al. |
| 4,670,007 A | 6/1987 | Wheeldon et al. |
| 5,042,494 A | 8/1991 | Alfano |
| 5,377,676 A * | 1/1995 | Vari et al. ................ 600/317 |
| 5,865,754 A | 2/1999 | Sevick-Muraca et al. |
| 5,865,829 A | 2/1999 | Kitajima |
| 6,372,895 B1 * | 4/2002 | Bentsen et al. ............. 536/4.1 |
| 6,405,070 B1 | 6/2002 | Banerjee |
| 2005/0043674 A1 | 2/2005 | Blair et al. |
| 2005/0085732 A1 | 4/2005 | Sevick-Muraca et al. |

FOREIGN PATENT DOCUMENTS

| JP | 54-096284 A | 7/1979 |
| JP | 61-085960 A | 5/1986 |
| JP | 01-317452 A | 12/1989 |
| JP | 7-313137 | 12/1995 |
| JP | 08-224208 | 9/1996 |
| JP | 10-201707 | 8/1998 |
| JP | 11-178568 | 7/1999 |

(Continued)

OTHER PUBLICATIONS

English-language Abstract of International PCT Patent Publication No. WO 97/34648, dated Sep. 25, 1997.

(Continued)

*Primary Examiner* — Michael P Stafira
(74) *Attorney, Agent, or Firm* — Scully, Scott, Murphy & Presser, P.C.

(57) ABSTRACT

A fluorescent agent accumulation concentration measuring apparatus is configured to include a single-wavelength LED to radiate excitation light to a test bottle loaded in the inside, a barrier filter to transmit only fluorescence from the test bottle, a photoreceptor to receive the fluorescence through the barrier filter and output an electric signal, a detection processing circuit to conduct signal processing of the electric signal from the photoreceptor and detect the fluorescence intensity, and an operation circuit 26 to compare the detection result from the detection processing circuit with an analytical pattern stored in a pattern storage portion and calculate the peak time of the accumulation concentration in a tissue of a sample in the test bottle.

7 Claims, 20 Drawing Sheets

FOREIGN PATENT DOCUMENTS

| | | |
|---|---|---|
| JP | 11-183382 | 7/1999 |
| JP | 2000-507129 | 6/2000 |
| JP | 2003-290345 A | 10/2003 |
| JP | 2004-358065 A | 12/2004 |

OTHER PUBLICATIONS

Muguruma, Naoki, et al., "Labeled Carcinoembryonic Antibodies Excitable by Infrared Rays: A Novel Diagnostic Method for Micro Cancers in the Digestive Tract", Internal Medicine (1999), vol. 38, No. 7, pp. 537-542.

Official Action dated Jan. 19, 2010 received from the Japanese Patent Office.

Official Action dated Dec. 7, 2010 received from the Japanese Patent Office.

U.S. Office Action issued in corresponding U.S. Appl. No. 11/327,866, mailed Apr. 29, 2010.

* cited by examiner

FIG.11

```
                                    /-11
┌─────────────────────────────────────────────────────────────┐
│   Oct.24.2004         ID=12345678                           │
│                                                             │
│   REAGENT: XYZ001     THE NUMBER OF MEASUREMENT: 1 TIME     │
│                                                             │
│ MEASUREMENT RESULT: PLEASE HAVE RE-INSPECTION AT 9 P.M.     │
└─────────────────────────────────────────────────────────────┘
```

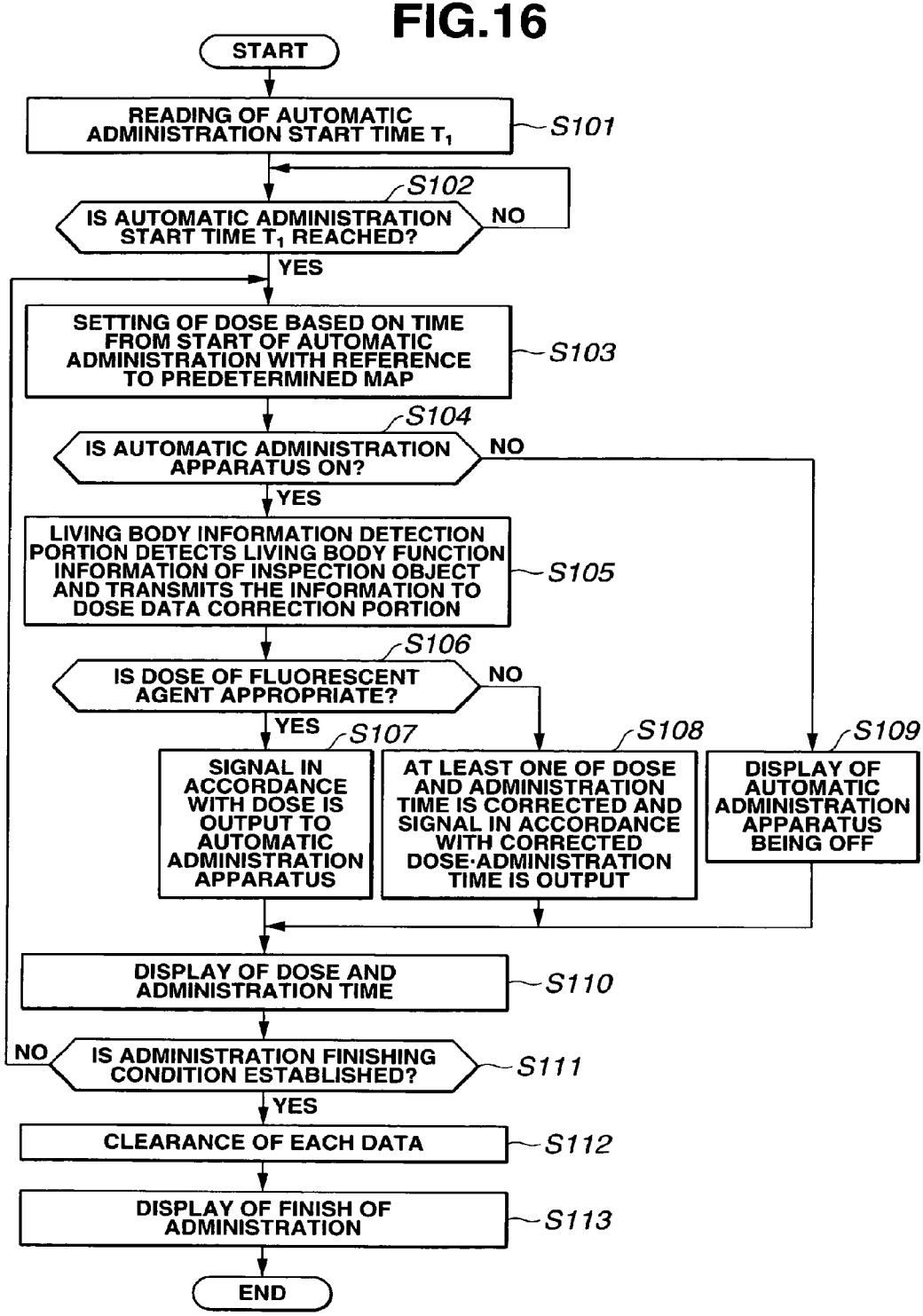

FLUORESCENT AGENT CONCENTRATION MEASURING APPARATUS, DOSE CONTROL APPARATUS, ADMINISTRATION SYSTEM, FLUORESCENT AGENT CONCENTRATION MEASURING METHOD, AND DOSE CONTROL METHOD

This application is a continuation application of U.S. patent application Ser. No. 11/327,866, filed Jan. 9, 2006, which claims benefit of Japanese Patent Application No. 2005,004577 filed on Jan. 11, 2005, Japanese Patent Application No. 2005-291599 filed on Oct. 4, 2005 and Japanese Patent Application No. 2005-370668 filed on Dec. 22, 2005, the entire contents of each of which are incorporated herein by reference.

BACKGROUND OF THE INVENTION

1. Field of the Invention

The present invention relates to a fluorescent agent concentration measuring apparatus and a fluorescent agent concentration measuring method, wherein the concentration of a fluorescent agent in a living body is measured, and furthermore, to a dose control apparatus, an administration system, and a dose control method, wherein a fluorescence state of an inspection object is maintained favorably when a fluorescent drug is administered by using the fluorescent agent concentration measuring apparatus and fluorescence observation is conducted with a fluorescence endoscope or the like.

2. Related Art Statement

In recent years, a technology in which autofluorescence from a living body or fluorescence from a drug injected into a living body is detected as a two-dimensional image, and degeneration of a living body tissue and a status of disease, e.g., a cancer, (for example, type of disease and range of humectation) are diagnosed from the fluorescence figure thereof is disclosed in U.S. Pat. No. 4,556,057 and U.S. Pat. 5,042,494.

When light is radiated to a living body tissue, fluorescence with a wavelength longer than that of the excitation light is emitted. Examples of phosphors in the living body include NADH (nicotinamide adenine nucleotide), FMN (flavin mononucleotide), and pyridine nucleotide. Recently, the correlations between these living-body internal cause substances and diseases are becoming clear.

Furthermore, fluorescent agents, e.g., HpD (hematoporphyrin), Photofrin, and ALA (δ-amino levulinic acid), serving as drugs to emit fluorescence have a property of accumulating on a cancer and, therefore, disease sites can be diagnosed by injecting these fluorescent agents into living bodies and conducting fluorescence observation.

Technologies for endoscopically diagnosing a lesion site based on the above-described fluorescence include fluorescence observation endoscope apparatuses disclosed in, for example, Japanese Unexamined Patent Application Publication No. 8-224208 and the like.

In recent years, a diagnosis and treatment method in which a fluorescent drug having an affinity for lesions, e.g., a cancer, is administered beforehand in the body of an inspection object, excitation light to excite the drug is radiated and, thereby, fluorescence from the drug accumulated on the lesion is detected has been noted.

For example, Japanese Unexamined Patent Application Publication No. 10-201707 discloses an endoscope apparatus in which the light emitted from a lamp is adjusted to have a wavelength band including infrared excitation light and visible light by a band-pass filter, and is radiated through a light guide fiber of the endoscope to an inspection object administered with a indocyanine green derived labeled antibody which is excited in an infrared region and emits fluorescence, so that the diagnosis and treatment can be conducted while a fluorescence figure and a normal image by the visible light are displayed on a monitor.

Furthermore, PCT Japanese Translation Patent Publication No. 2000-507129 discloses an intraveneous injection control apparatus in which a calibrated coding device, e.g., a calibrated rotatable knob, capable of setting variably a desired value and a microcontroller provided with a program of pharmacological model are included and the concentration of a drug fluid in the blood or the like is kept constant based on the pharmacological model during execution of injection by the user.

SUMMARY OF THE INVENTION

A fluorescent agent concentration measuring apparatus according to the present invention has a feature that the peak timing of accumulation concentration of a fluorescent agent on a living body tissue is calculated appropriately. A dose control apparatus according to the present invention has a feature that a favorably stable fluorescence observation under fluorescence intensity close to its peak is made possible, and an improvement in diagnostic performance and a reduction of observation time can be achieved.

The fluorescent agent concentration measuring apparatus of the present invention includes an excitation light source to radiate excitation light to a sample containing a body fluid taken from a living body administered with a fluorescent drug, the excitation light allowing the drug to emit fluorescence; a fluorescence detection portion to detect the fluorescence; a fluorescent agent concentration calculation portion to calculate the concentration of the drug in the living body, based on a detection signal from the fluorescence detection portion; and a peak time estimation portion to estimate the peak time of the concentration of the drug in the living body tissue, based on the elapsed time after administration of the drug to the living body and the calculated concentration of the drug.

The dose control apparatus of the present invention includes the fluorescent agent concentration measuring apparatus; an administration start judgment portion to judge whether a predetermined time has elapsed or not and to judge the start of administration of the drug when the predetermined time has elapsed; a dose setting portion to set at least one of the dose and the administration time of the drug, based on the predetermined dose information of the drug after the judgment of the start of administration by the administration start judgment portion; an output apparatus to perform at least one of functions of allowing a monitor portion for monitoring to display the dose and allowing an automatic administration apparatus to administer the drug, based on the dose of the drug set by the dose setting portion; and a living body information detection portion to detect living body function information of the living body and to transmit the living body function information to the dose setting portion.

Other features and advantages will be made clear by the following description.

BRIEF DESCRIPTION OF THE DRAWINGS

FIG. 11 is a diagram showing a second display example of the display portion shown in FIG. 1.

FIG. 16 is a flow chart of a dose control program in the dose control apparatus shown in FIG. 13.

DETAIL DESCRIPTION OF THE PREFERRED EMBODIMENT

The embodiments of the present invention will be described below with reference to the drawings.

First Embodiment

Figure 1:
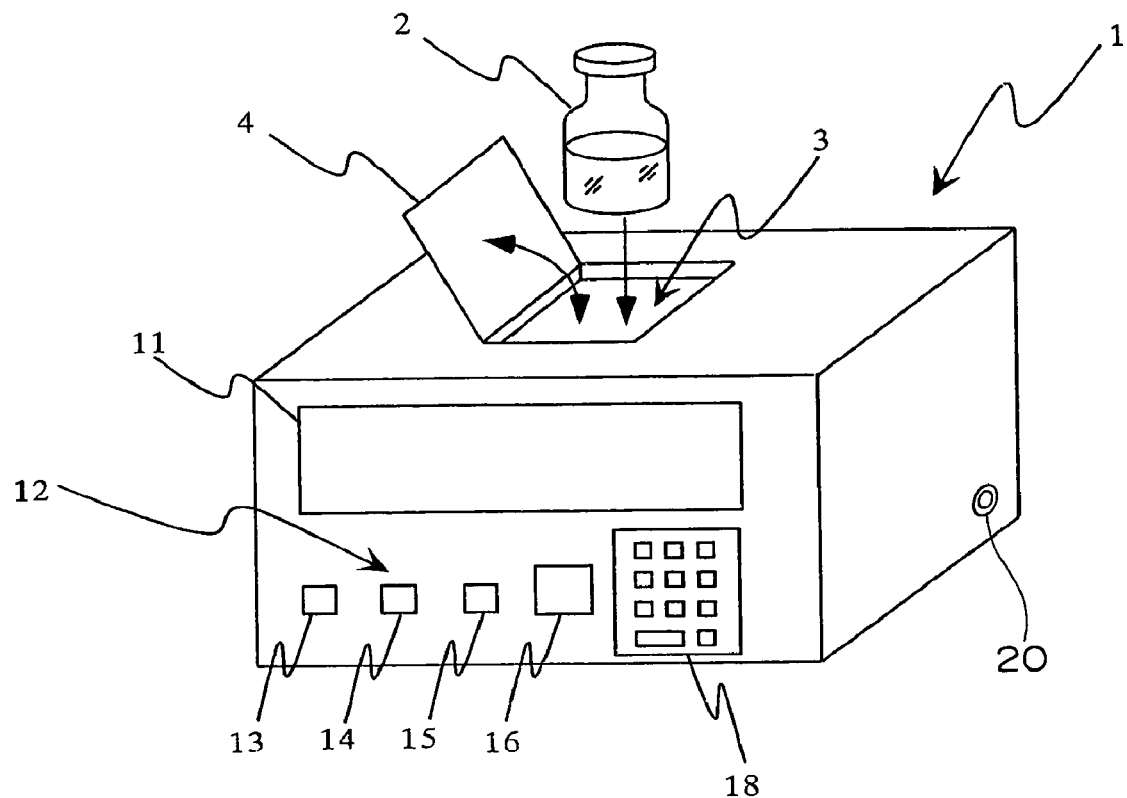
FIG. 1 is an external view showing the appearance of a fluorescent agent concentration measuring apparatus according to a first embodiment of the present invention.
Figure 2:
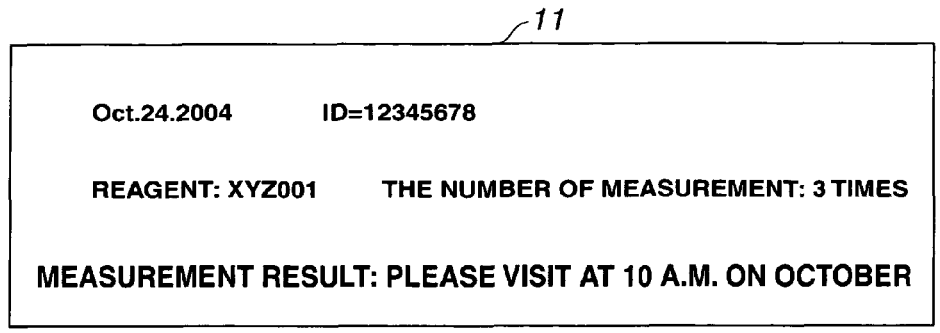
FIG. 2 is a diagram showing a first display example of a display portion shown in FIG. 1.
Figure 3:
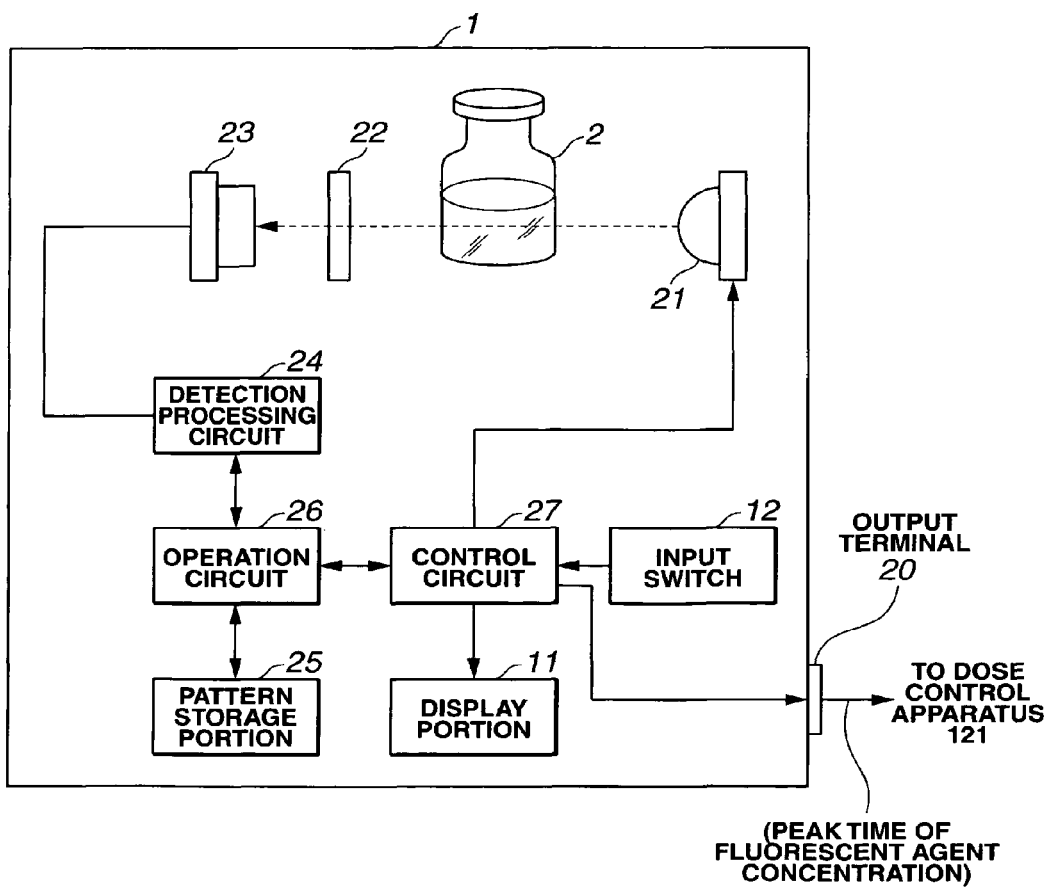
FIG. 3 is a block diagram showing the configuration of the fluorescent agent concentration measuring apparatus shown in FIG. 1.
Figure 4:
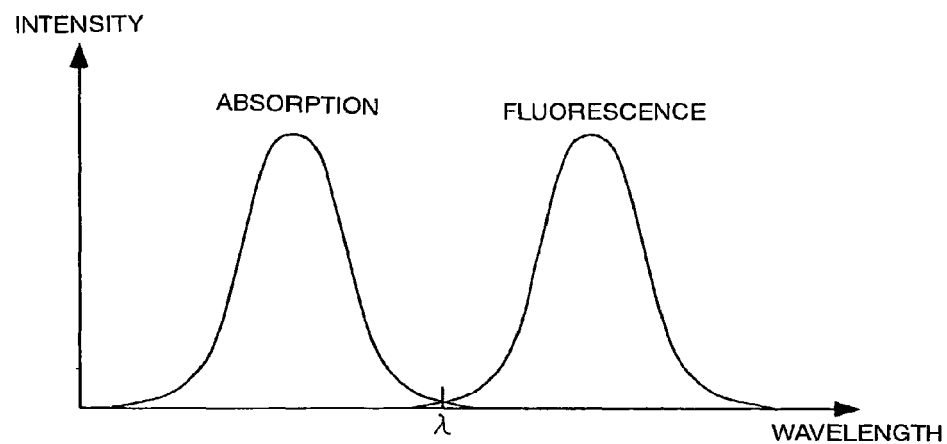
FIG. 4 is a diagram showing light absorption and light emission characteristics of a sample in a test bottle shown in FIG. 2.
Figure 5:
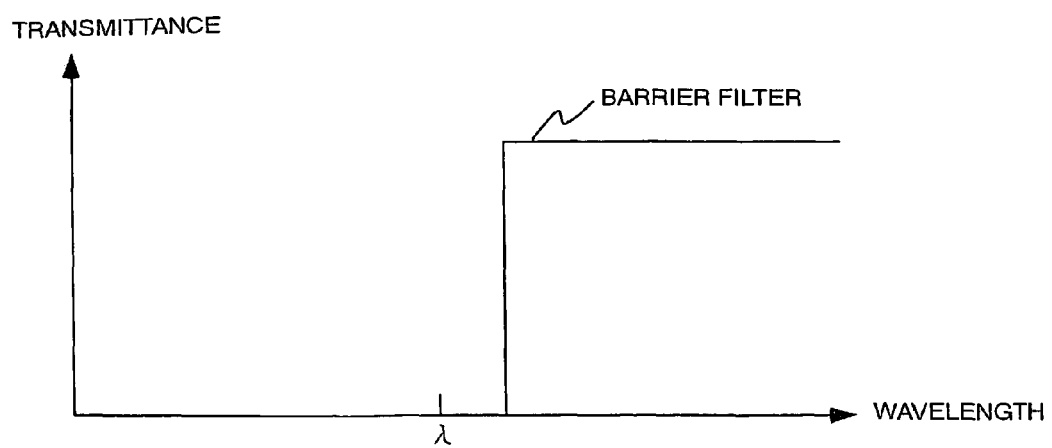
FIG. 5 is a diagram showing a transmission characteristic of a barrier filter shown in FIG. 2.
Figure 6:
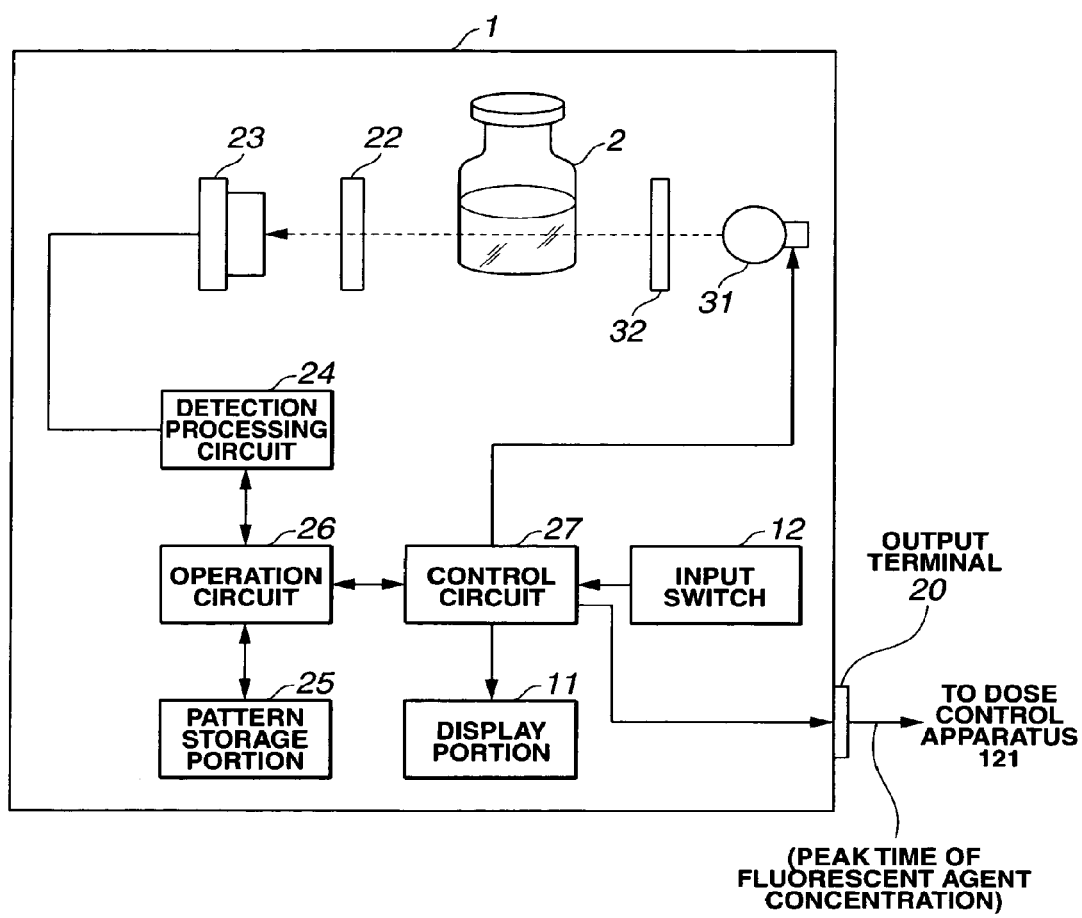
FIG. 6 is a block diagram showing the configuration of a modification of the fluorescent agent concentration measuring apparatus shown in FIG. 1.
Figure 7:
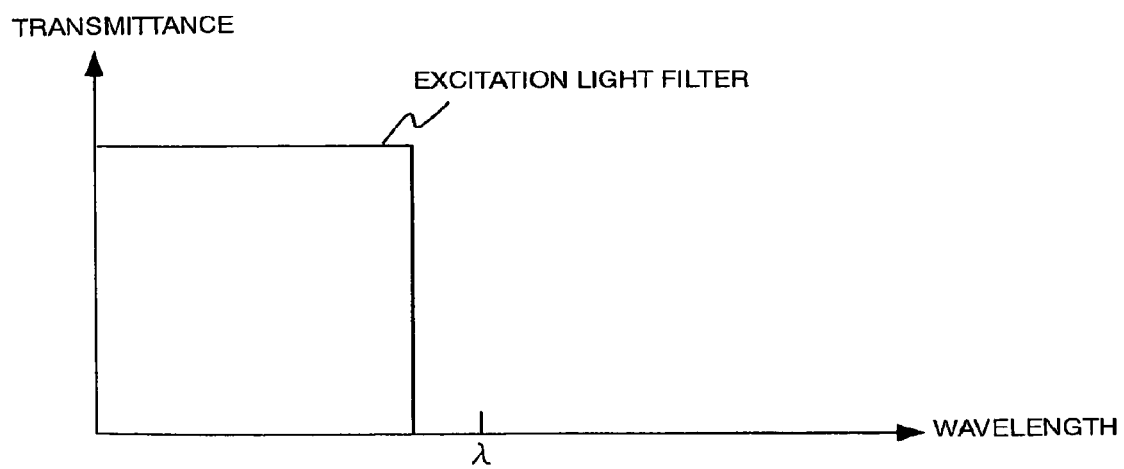
FIG. 7 is a diagram showing a transmission characteristic of an excitation light filter shown in FIG. 6.
Figure 8:
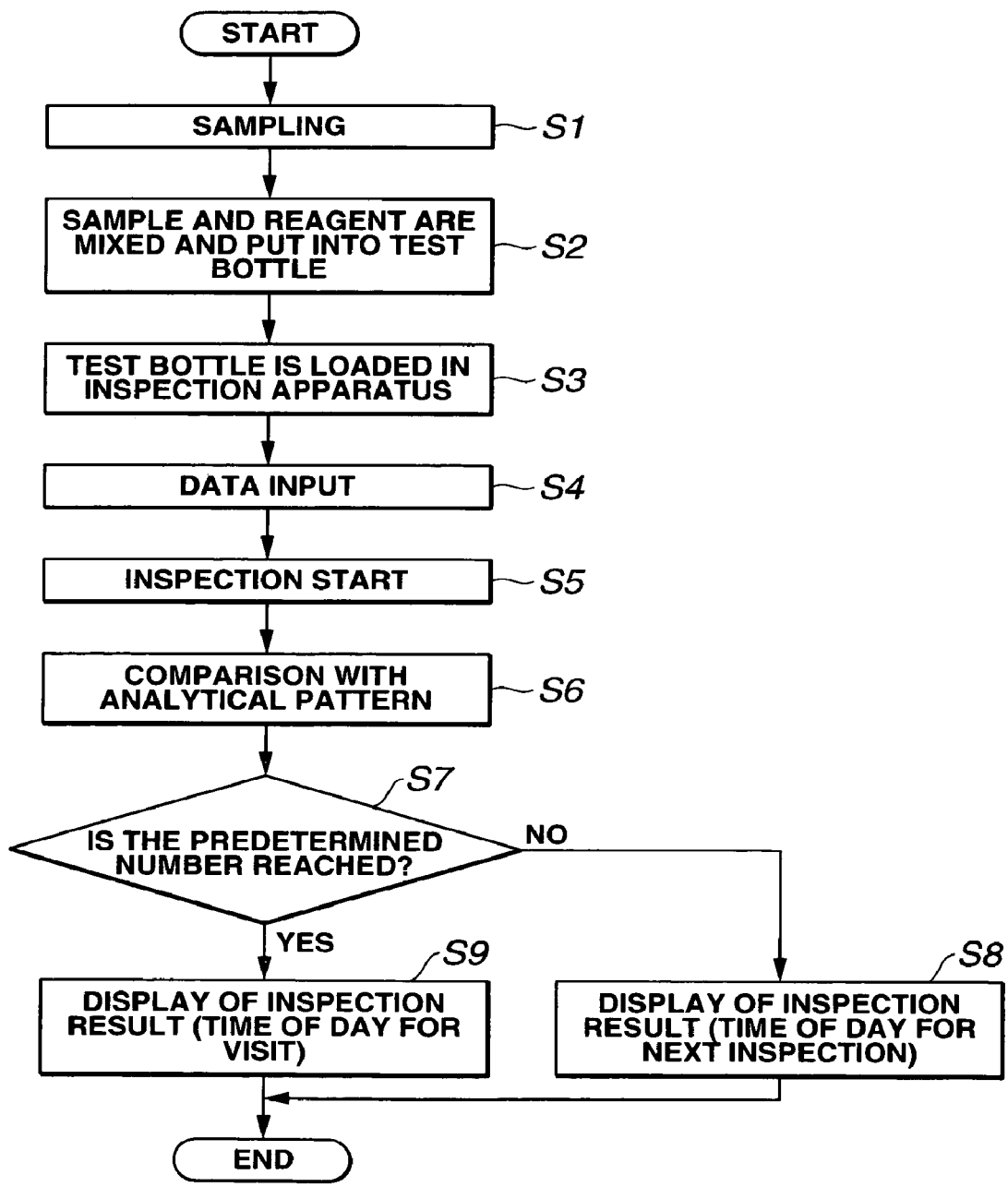
FIG. 8 is a flow chart for explaining operations of the fluorescent agent concentration measuring apparatus shown in FIG. 2.
Figure 9:
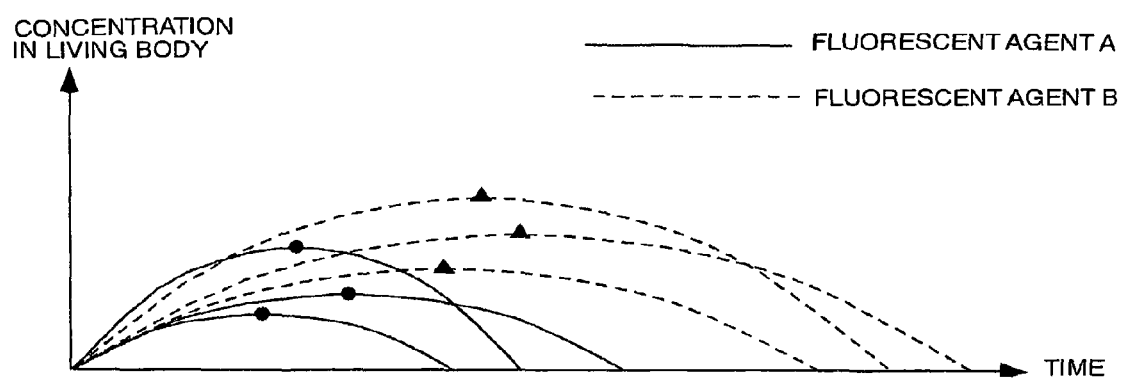
FIG. 9 is a diagram showing an example of an analytical pattern group stored in a pattern storage portion shown in FIG. 2 and composed of a plurality of analytical patterns reflecting the individual difference on a fluorescent agent basis.
Figure 10:
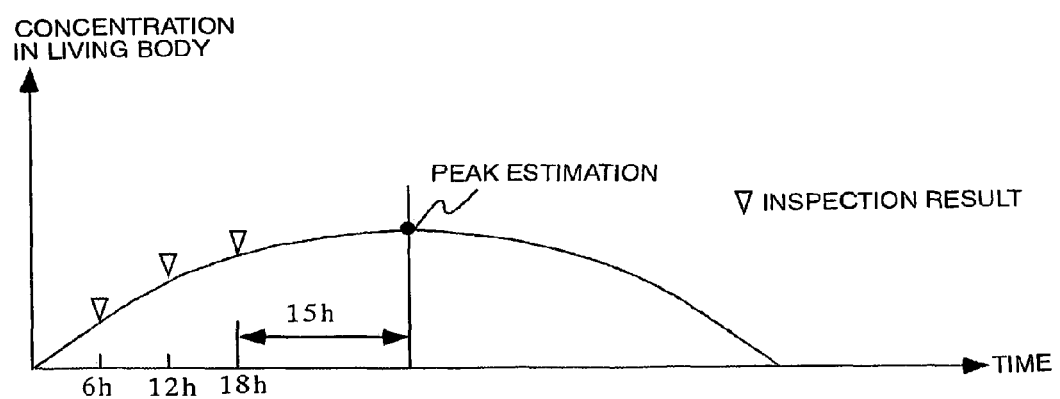
FIG. 10 is a diagram for explaining processing for comparing with each analytical pattern of the analytical pattern group, shown in FIG. 8.

FIG. 1 to FIG. 11 relate to a first embodiment of the present invention. FIG. 1 is an external view showing the appearance of a fluorescent agent concentration measuring apparatus. FIG. 2 is a diagram showing a first display example of a display portion shown in FIG. 1. FIG. 3 is a block diagram showing the configuration of the fluorescent agent concentration measuring apparatus shown in FIG. 1. FIG. 4 is a diagram showing light absorption and light emission characteristics of a sample in a test bottle shown in FIG. 2. FIG. 5 is a diagram showing a transmission characteristic of a barrier filter shown in FIG. 2. FIG. 6 is a block diagram showing the configuration of a modification of the fluorescent agent concentration measuring apparatus shown in FIG. 1. FIG. 7 is a diagram showing a transmission characteristic of an excitation light filter shown in FIG. 6. FIG. 8 is a flow chart for explaining operations of the fluorescent agent concentration measuring apparatus shown in FIG. 2. FIG. 9 is a diagram showing an example of an analytical pattern group stored in a pattern storage portion shown in FIG. 2 and composed of a plurality of analytical patterns reflecting the individual difference on a fluorescent agent basis. FIG. 10 is a diagram for explaining processing for comparing with each analytical pattern of the analytical pattern group, shown in FIG. 8. FIG. 11 is a diagram showing a second display example of the display portion shown in FIG. 1.

As shown in FIG. 1, the fluorescent agent concentration measuring apparatus 1 of the present embodiment is portable and can be lent to a patient. The patient measures the concentration of the administered fluorescent agent in the living body tissue with the apparatus by oneself at home or the like. Here, the fluorescent agent refers to a drug which emits fluorescence.

The fluorescent agent concentration measuring apparatus 1 has a loading portion (container loading portion) 3, while a test bottle 2 containing a sample including saliva, urine, blood, or the like of the patient is loaded removably in the inside of the loading portion 3. A light shield cover (light shield portion) 4 to block external light when the test bottle 2 is loaded in the inside is disposed on the upper surface of this loading portion 3.

A display portion 11 composed of, for example, LCD and the like, to display various data and an input switch portion 12 to input various data are disposed on the front surface of the fluorescent agent concentration measuring apparatus 1. The input switch portion 12 is composed of, for example, a date setting switch 13 to designate a date, a patient ID setting switch 14 to designate the ID of the patient, a fluorescent agent setting switch 15 to designate the fluorescent agent administered to the patient, a start switch 16 to instruct the start of measurement, and a keyboard portion 18 capable of inputting a character string, e.g., numbers or an alphabet, and the like. An output terminal 20 to output signals of a peak time of the fluorescent agent concentration and the like is disposed on a side surface or a back of the fluorescent agent concentration measuring apparatus 1.

As shown in FIG. 2, the data of date, the patient ID, the fluorescent agent name, and the like input by using the input switch portion 12, as well as the number of inspections conducted by the patient by oneself and the inspection results, are displayed on the display portion 11.

Specifically, as shown in FIG. 3, the fluorescent agent concentration measuring apparatus 1 is configured to include a single-wavelength LED (single-wavelength laser light source) 21 serving as an excitation light source to radiate excitation light to the test bottle 2 loaded in the inside, a barrier filter (optical filter) 22 to transmit only fluorescence from the test bottle 2, a photoreceptor (fluorescence detection portion) 23 to receive fluorescence through the barrier filter 22 and output an electric signal, a detection processing circuit (fluorescence detection portion) 24 to conduct signal processing of the electric signal from the photoreceptor 23 and detect the fluorescence intensity, an operation circuit (fluorescent agent concentration calculation portion) 26 to compare the detection result from the detection processing circuit 24 with an analytical pattern (described below) stored in a pattern storage portion 25 serving as a curve data storage portion and calculate the peak time of the concentration in a tissue of the sample in the test bottle 2, and a control circuit 27 to control these various circuits, the display portion 11, and the input switch portion 12.

As shown in FIG. 4, a predetermined wavelength of $\gamma$ is positioned at a border. The sample in the test bottle 2 absorbs excitation light with a wavelength shorter than the wavelength of $\gamma$, and emits fluorescence with a wavelength longer than the wavelength of $\gamma$ through excitation by the excitation light.

Therefore, the excitation light with a single wavelength shorter than the wavelength of $\gamma$ is radiated from the single-wavelength LED 21 to the sample in the test bottle 2, the light is received by the photoreceptor 23 through the barrier filter 22 having a transmission characteristic shown in FIG. 5 and, thereby, only the fluorescence from the sample in the test bottle 2 is detected by the photoreceptor 23.

Alternatively, as shown in FIG. 6, a white lamp (for example, a xenon lamp) 31 can be used as a white light source in place of the single-wavelength LED 21. In this configuration, only the light with a wavelength shorter than the wavelength of $\gamma$ may be radiated to the test bottle 2 by disposing an excitation light filter (transmission filter) 32 having a transmission characteristic shown in FIG. 7 in between the white lamp 31 and the test bottle 2, and the fluorescence may be received by the photoreceptor 23 through the barrier filter 22.

The operations of the thus configured present embodiment will be described.

When a fluorescent agent is administered into the living body of the patient in a hospital or the like which the patient visits, the patient is lent the fluorescent agent concentration measuring apparatus 1 of the present embodiment from the hospital or the like, and disposes this fluorescent agent concentration measuring apparatus 1 at home or the like. At this time, the test bottle 2 and a predetermined reagent to be mixed to a sample, e.g., saliva, urine, or blood, are supplied together with the fluorescent agent concentration measuring apparatus 1 from the hospital or the like to the patient.

The fluorescent agent concentration measuring apparatus 1 disposed at home or the like as described above is used. As shown in FIG. 8, at the inspection time of day previously instructed by the hospital or the like, the patient takes a sample from saliva, urine, blood, or the like in step S1, and mix the sample and the supplied predetermined reagent so as to put into the test bottle 2 in step S2. In the case where the fluorescent agent in the sample is a fluorescent agent of PeT (Photo-induced Electron Transfer) system, this predetermined sample is a drug to activate the fluorescent agent in the sample.

In step S3, the test bottle containing the sample is loaded in the loading portion 3 of the fluorescent agent concentration measuring apparatus 1, the light shield cover 4 is closed and, thereby, the test bottle 2 is disposed in the inside of the fluorescent agent concentration measuring apparatus 1 while being shielded from external light.

Subsequently, the following processing is executed under the control of the control circuit 27. That is, in step S4, various data, e.g., the data of date, the patient ID, and the fluorescent agent name, are input by using the input switch portion 12 (the date setting switch 13, the patient ID setting switch 14, the fluorescent agent setting switch 15, and the keyboard portion 18).

Although not shown in the drawing, for example, an RF-ID tag, in which the patient ID, the fluorescent agent name, and the like are recorded, may be disposed on the test bottle 2 and, in addition, an RF-ID communication device may be disposed in the fluorescent agent concentration measuring apparatus 1, so that the patient ID and the fluorescent agent name recorded in the RF-ID tag may be taken into the fluorescent agent concentration measuring apparatus 1 by radio.

In step S5, the start switch 16 of the input switch portion is pushed down and, thereby, an inspection of the fluorescent agent concentration of the sample in the test bottle 2 is started.

When the inspection is started, the excitation light is radiated from the single-wavelength LED 21 to the test bottle 2. The fluorescence emitted from the excited sample in the test bottle 2 is received by the photoreceptor 23 through the barrier filter 22. The electric signal from the photoreceptor 23 is output to the detection processing circuit 24.

In step S6, the intensity of the fluorescence from the excited sample in the test bottle 2 and the inspection time of day are compared with the analytical pattern stored in the pattern storage portion 25 by the operation circuit 26.

As shown in FIG. 9, since the concentrations of the fluorescent agents in the living body are different on a type of the fluorescent agent basis and, furthermore, the concentration varies due to the individual difference even when the fluorescent agent is the same. Consequently, an analytical pattern group composed of a plurality of analytical patterns reflecting the individual difference on a fluorescent agent basis is stored in the pattern storage portion 25, and the comparison with the sample is conducted by using a group of these analytical patterns. As an example, FIG. 9 shows two groups of analytical patterns for a fluorescent agent A (solid line) and a fluorescent agent B (broken line), each group composed of three analytical patterns based on the individual difference.

As described above, since the concentration of the fluorescent agent in the living body varies depending on not only the type of fluorescent agent administered to the patient, but also the individual difference of patient, the times of day at which the concentrations of the fluorescent agents in the living body reach their peaks are different. In FIG. 9, peak points of the fluorescent agent A (solid line) are indicated by black circles and peak points of the fluorescent agent B (broken line) are indicated by black triangles.

Therefore, in the comparison with the analytical pattern in step S6, the analytical pattern group to be compared is selected based on the type of fluorescent agent (fluorescent agent name) and, as shown in FIG. 10, the intensities of fluorescence (inspection results) from the sample and each analytical pattern of the analytical pattern group at the inspection time of day are compared with each other.

The above-described comparison is conducted a plurality of times, e.g., three times, and thereby, the peak time of day of the concentration of the fluorescent agent in the living body is estimated. Therefore, it is judged whether or not the number of inspections has reached a predetermined number in step S7. When the number is not reached, in step S8 as shown in FIG. 11, the time of day for the next inspection is displayed on the display portion 11 as the inspection result, and the processing is finished. When the number of inspections has reached a predetermined number and the peak time of day of the concentration of the fluorescent agent in the living body is estimated, as shown in FIG. 2, the time of day for visit is displayed as the inspection result in step S9, and the processing is finished. The above-described peak time estimation processing is conducted by a peak time estimation portion built in the control circuit 27.

In step S9, the peak time of day of the concentration of the fluorescent agent in the living body may be output from the control circuit 27 to the output terminal 20. The output terminal 20 is to be connected to, for example, an apparatus for administering the fluorescent agent into the living body. In this manner, the apparatus for administering the fluorescent agent into the living body, for example, a dose control apparatus 121 described below, can control the administration start time, the dose, and the like of the fluorescent agent, based on the peak information attained through the output terminal 20.

Here, the estimation of the peak time of the concentration of the fluorescent agent in the living body will be described in detail. The inspection times of day are different depending on the types of fluorescent agent. The first inspection time of day is instructed from the hospital or the like, based on the administration of the fluorescent agent. The time of day for the following inspection is the time of day a predetermined time interval after the first inspection time.

When some fluorescent agent is administered, by conducting the inspection a plurality of times at a predetermined time interval, for example, 3 times at a time interval of 6 hours, from the administration time of the fluorescent agent, it is made clear which analytical pattern is applicable to the intensities of fluorescence (inspection results) from the sample at the plurality of inspection times of day by the comparison. Consequently, the peak of the resulting applicable analytical pattern is assumed as the peak time of day of the concentration of this fluorescent agent in the living body.

For example, FIG. 10 is an example of 3 times at a time interval of 6 hours from the administration time of day of the fluorescent agent, wherein it is estimated that the peak time of day of the concentration of the fluorescent agent in the living body becomes the time of day 15 hours elapsed from the last administration time of day.

As described above, in the present embodiment, since the fluorescent agent concentration measuring apparatus 1 is portable and can be lent to a patient, the patient is not required to stay in the hospital until the concentration of the fluorescent agent in the living body tissue reaches its peak. As a result, the peak time of day of the concentration of the fluorescent agent in the living body tissue can be estimated only by measuring the fluorescent agent concentration in the sample of saliva, blood, or the like at home or the like at a predetermined time interval with the fluorescent agent concentration measuring apparatus 1. Therefore, it is possible to encourage the patient to visit the hospital by notifying the patient of this peak time of day.

Second Embodiment

Figure 12:
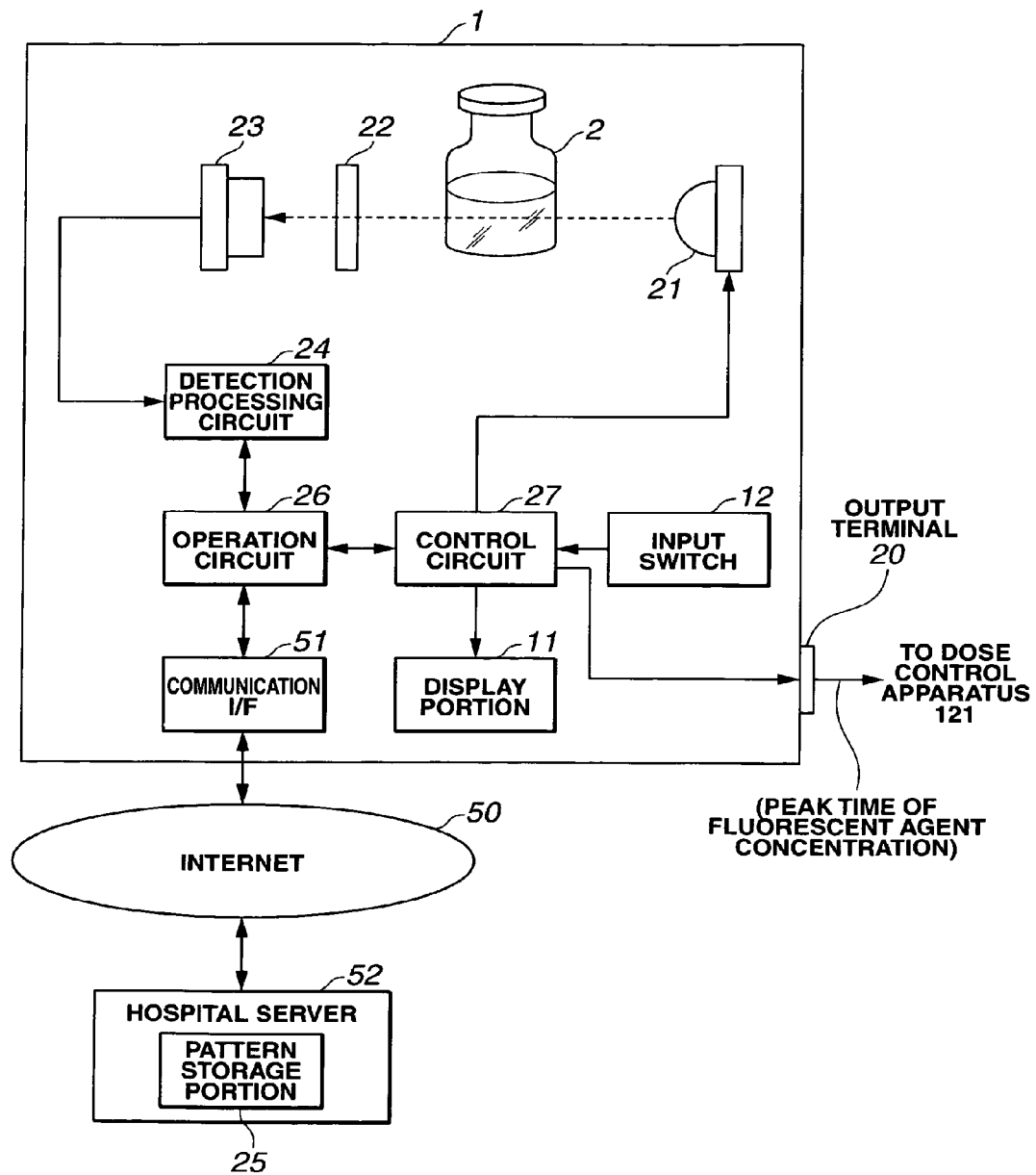
FIG. 12 is a block diagram showing the configuration of a fluorescent agent concentration measuring apparatus according to a second embodiment of the present invention.

FIG. 12 is a block diagram showing the configuration of a fluorescent agent concentration measuring apparatus according to a second embodiment of the present invention.

Since the second embodiment is substantially the same as the first embodiment, only the different points are described, and the same configurations are indicated by the same reference numerals as those set forth above and explanations thereof will not be provided.

As shown in FIG. 12, in the configuration of the present embodiment, a communication I/F 51 serving as a communication portion capable of communicating with a wide-area network, e.g., Internet 50, is disposed in a fluorescent agent concentration measuring apparatus 1 and a pattern storage portion 25 is disposed in a hospital server 52 serving as an in-hospital external server connected to the Internet 50. Other configurations and operations are equal to those in the first embodiment.

The configuration of the present embodiment exhibits more outstanding portability since there is no need to dispose the pattern storage portion 25 in the inside of the fluorescent agent concentration measuring apparatus 1. Since the information of the intensity of fluorescence (inspection result) from the sample of the patient can be accumulated in the hospital server 52, it becomes possible to generate various analytical patterns based on the information of the intensity of fluorescence (inspection result) and store in the pattern storage portion 25 serving as a curve data storage portion. It is also possible to omit the operation circuit 26 by allowing the hospital server 52 to have an arithmetic function of the operation circuit 26.

In the fluorescence observation with a fluorescence endoscope or the like through administration of a fluorescent drug by using the fluorescent agent concentration measuring apparatuses 1 explained in the above-described first and second embodiments, the following embodiments can be adopted as a dose control apparatus to maintain the fluorescent state of the inspection object at a favorable state and an administration system including the same.

Third Embodiment

Figure 13:
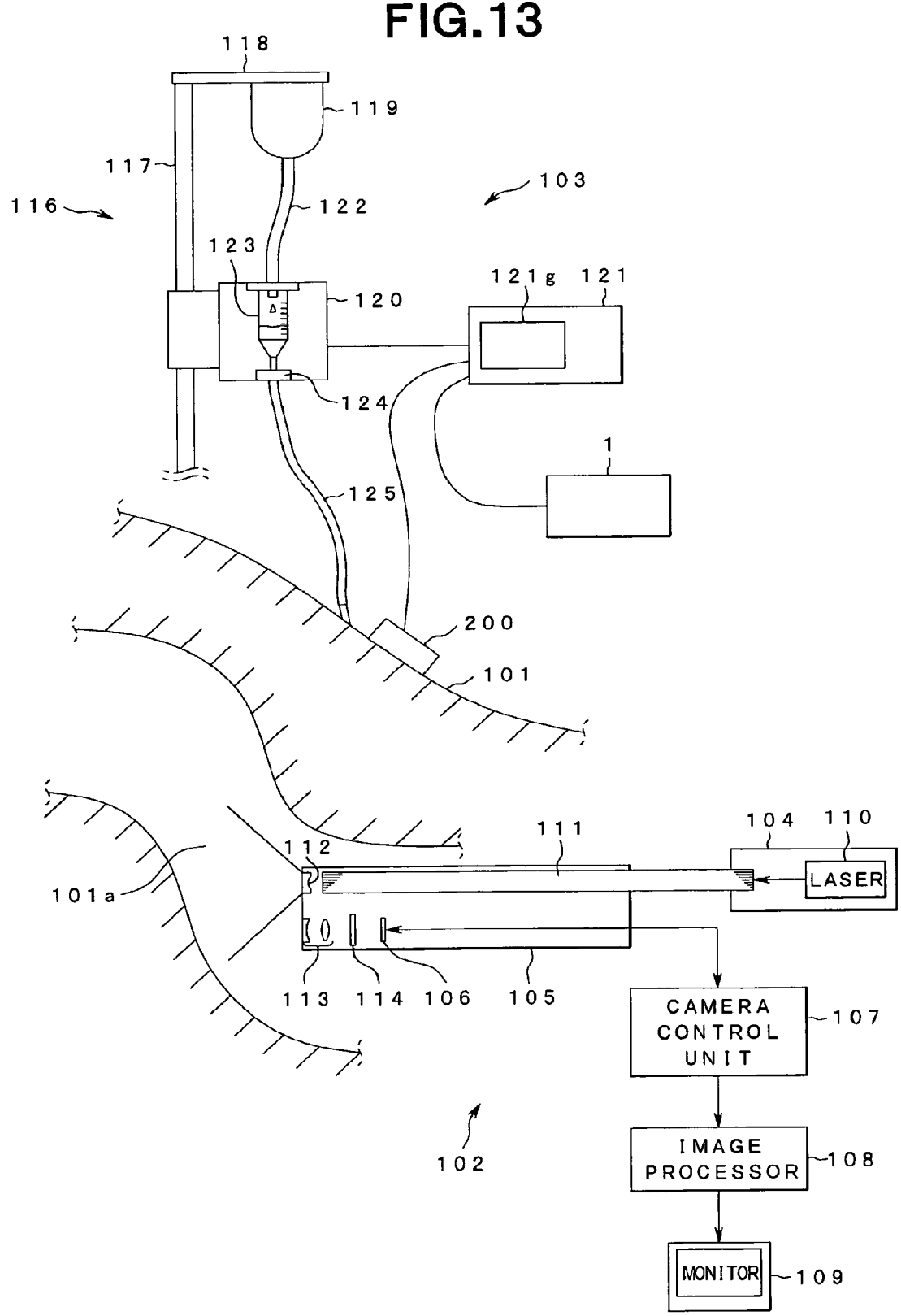
FIG. 13 is an explanatory diagram of an entire system when a fluorescence observation is conducted with an endoscope by using a dose control apparatus according to a third embodiment of the present invention.
Figure 14:
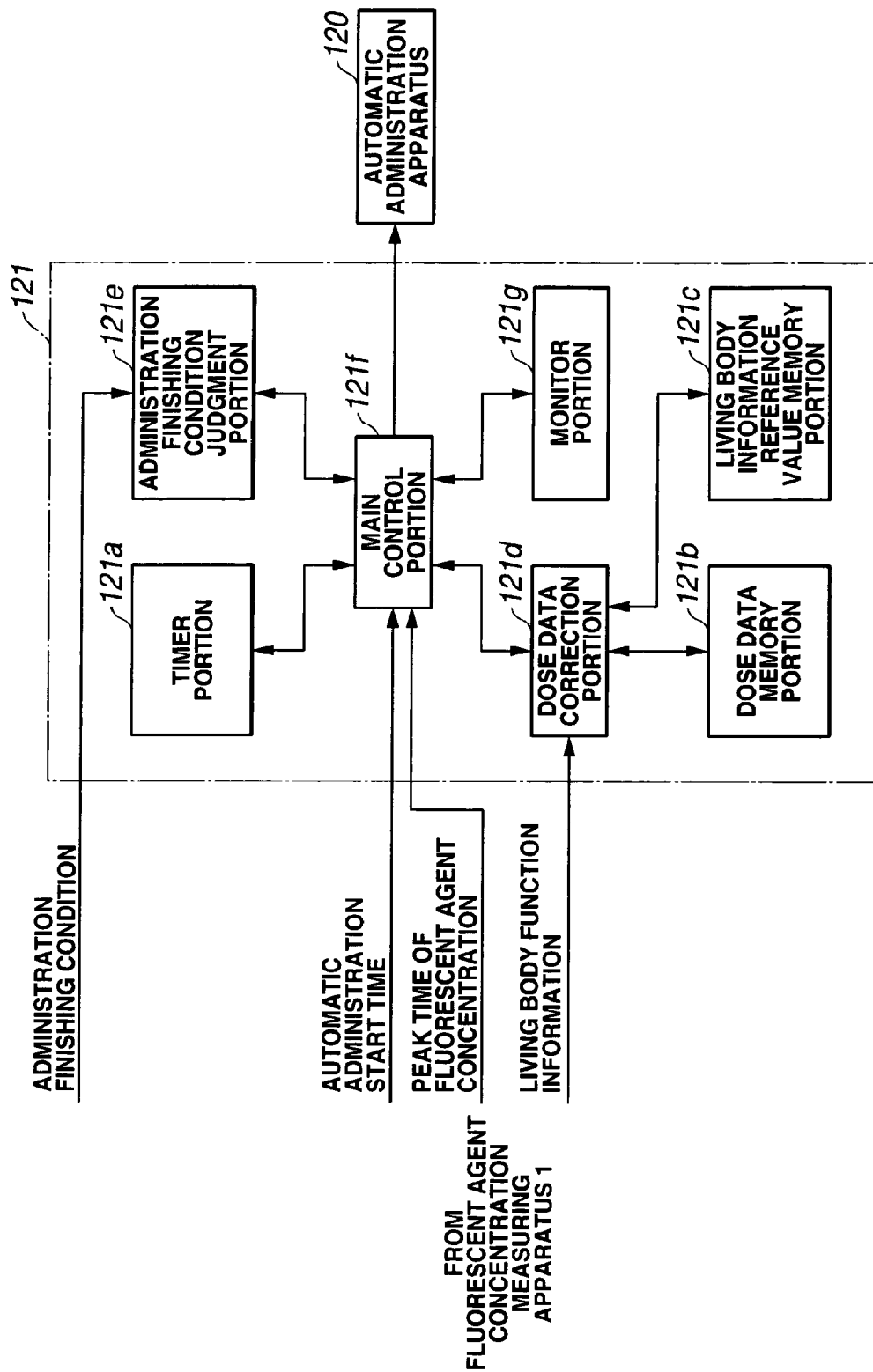
FIG. 14 is a functional block diagram of the dose control apparatus shown in FIG. 13.
Figure 17:
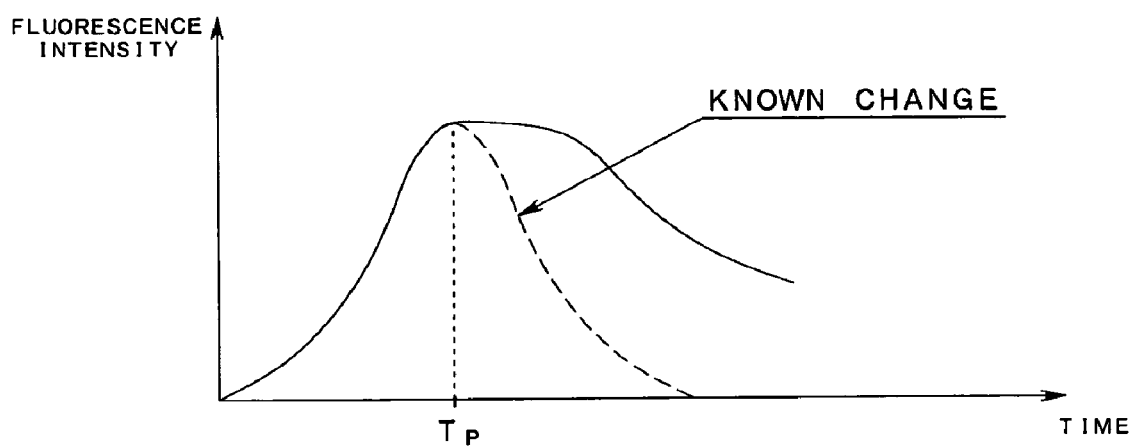
FIG. 17 is an explanatory diagram of a fluorescence intensity improvement attained by dose control in the dose control apparatus shown in FIG. 13.

FIG. 13 to FIG. 17 show a third embodiment of the present invention. FIG. 13 is an explanatory diagram of an entire system when a fluorescence observation is conducted with an endoscope by using a dose control apparatus. FIG. 14 is a functional block diagram of the dose control apparatus. FIG. 15A to FIG. 15D are explanatory diagrams of dose information maps of a fluorescent agent. FIG. 16 is a flow chart of a dose control program. FIG. 17 is an explanatory diagram of a fluorescence intensity improvement attained by dose control.

In FIG. 13, reference numeral 101 denotes an inspection object, e.g., a living body, to be subjected to a fluorescence observation by a fluorescence endoscope system 102. This inspection object is administered intravenously with a fluorescent drug (fluorescent agent, phosphor), e.g., a solution, in which an indocyanine green derived labeled antibody is dissolved, from a fluorescent agent administration system 103.

Since the indocyanine green derived labeled antibody described here as an example has an affinity for a lesion, e.g., a cancer, as described in PCT/WO96/23525, it accumulates in the lesion as time passes after being administered into a body. Since the structure is similar to that of indocyanine green (ICG) previously used for the inspection of the liver function, a high degree of safety is exhibited against the living body.

The fluorescence endoscope system 102 is primarily configured to include at least a light source 104 to emit excitation light, an endoscope 105 to introduce the excitation light into a living body lumen 101a and observe fluorescence emitted from the lesion site, a camera control unit 107 to drive a color image pickup device 106 built in the endoscope 105 so as to convert the fluorescence figure of the lesion to a video signal, an image processor 108 to process the video signal so as to facilitate discrimination between a lesion site and a normal portion, and a monitor 109 to display the output from the image processor 108 as an image.

The light source 104 incorporates a laser 110, e.g., excimer, He—Cd, or argon, to emit light in a blue or ultraviolet region.

The endoscope 105 is primarily configured to include a light guide 111 to lead laser light emitted from the laser 110 to the living body lumen 101a, a concave lens 112 to diffuse the laser light for illumination, objective lenses 113 to throw a fluorescence figure of the lesion site to the color image pickup device 106, and an optical filter 114 to transmit specific wavelengths of the fluorescence figure from the objective lenses 113. Here, the optical filter 114 has a predetermined transmission characteristic.

Although not shown in the drawing, light source 104 includes a xenon lamp for emitting white light and a switching portion to switch between the light from the laser and the light from the xenon lamp and supply to the light guide 111. Furthermore, the endoscope 105 incorporates an image pickup device, although not shown in the drawing, to pick up a figure by the white light.

Consequently, in the fluorescence endoscope system 102 having the above-described configuration, the laser light emitted from the laser 110 is incident on the light guide 111 built in the endoscope 105, and is led to the living body lumen 101*a*. The laser light is diffused by the concave lens 112 and is radiated to the living body lumen 101*a*. Fluorescence is emitted from a lesion site and a surrounding normal portion by this laser light, the resulting fluorescence passes objective lenses 113, and is projected on the color image pickup device 106 through the optical filter 114. The signal processing is conducted by the camera control unit 107 and the image processor 108 so as to display on the monitor 109, and fluorescence observation is conducted.

The fluorescence endoscope system 102 is not limited to that in the present third embodiment, and may have other configurations.

On the other hand, the fluorescent agent administration system 103 is primarily configured to include a drip infusion container 119 hung by a hanger component 118 at the top portion of a column 117 of an infusion stand 116, an automatic administration apparatus 120 serving as an automatic administration portion which is fixed to some midpoint of the column 117 of the same infusion stand 116 and administers a fluorescent drug (fluorescent agent, phosphor) supplied from the drip infusion container 119 to an inspection object 101, a dose control apparatus 121 to control the administration from the automatic administration apparatus 120 to the inspection object 101, a living body information detection portion 200 to detect the living body function information of the inspection object 101, and a fluorescent agent concentration measuring apparatus 1 to measure the concentration of the fluorescent agent in the living body.

An apparatus having a configuration and a function similar to those of the fluorescent agent concentration measuring apparatuses of the above-described first and second embodiments is applied to the fluorescent agent concentration measuring apparatus 1.

The above-described fluorescent drug (phosphor), e.g., a solution, in which an indocyanine green derived labeled antibody is dissolved, is encapsulated in the drip infusion container 119. The drip infusion container 119 is connected to the automatic administration apparatus 120 through a drip infusion tube 122 and, thereby, the fluorescent drug (phosphor) is supplied into a syringe 123 of the automatic administration apparatus 120.

The automatic administration apparatus 120 is, for example, an automatic drip infusion apparatus, and allows the fluorescent agent (phosphor) from the drip infusion container 119 to drip in the syringe 123. Subsequently, the fluorescent agent (phosphor) is administered to the vein of the inspection object 101 from the syringe 123 through a drip infusion tube 125. At this time, the intravenous administration of the fluorescent agent (phosphor) to the inspection object 101 at a desired flow rate can be conducted automatically or manually by variably adjusting the pushing force of a pushing component 124 disposed at the end portion of the syringe 123, based on the control signal from the dose control apparatus 121 or an operation by the operator.

The living body information detection portion 200 is to detect the living body information, and is disposed on a skin of the inspection object 101 while being electrically connected to the dose control apparatus 121. The living body information detection portion 200 detects the living body function information of the inspection object 101, and transmits the living body function information to the dose control apparatus 121. Here, the above-described living body function information refers to the information, such as the heart rate, the oxygen saturation, and the blood pressure, which relate to the metabolic information and can be detected through the skin of the inspection object 101. In the measurement of the living body function information, known measurement devices can be used appropriately as the living body information detection portion 200. For example, a measurement device, e.g., a pulse oxymeter, is used for the measurement of the oxygen saturation.

For the dose control apparatus 121, an automatic administration start time, the administration finishing condition, and the like are input by the operator, the living body function information is input by the living body information detection portion 200, and the dose in correspondence to the administration time is set based on a dose information map while following the dose control program described below. When the administration time is reached, the dose control apparatus 121 outputs an output signal in correspondence to the dose to the automatic administration apparatus 120 (in the case where automatic administration is conducted by the automatic administration apparatus 120) and, in addition, the dose, the administration time, and the like are displayed on a monitor portion 121*g*.

The dose control apparatus 121 corrects the dose or the administration timing of the fluorescent agent (phosphor) when the living body function information of the inspection object 101 detected by the living body information detection portion 200 varies during the automatic administration by the automatic administration apparatus 120.

In order to realize the above-described function, the dose control apparatus 121 is primarily configured to include, for example, a timer portion 121*a*, a dose data memory portion 121*b*, a living body information reference value memory portion 121*c*, a dose data correction portion 121*d*, an administration finishing condition judgment portion 121*e*, a main control portion 121*f*, and the monitor portion 121*g*, as shown in FIG. 14.

The timer portion 121*a* is a so-called timer, and an elapsed time is read by the main control portion 121*f*, as needed.

Figure 15A:
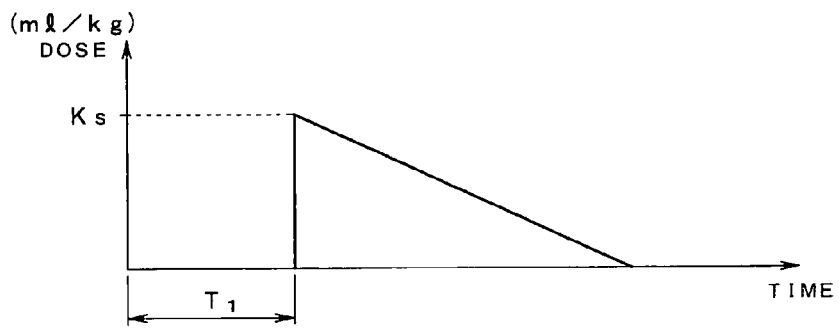
FIG. 15A to FIG. 15D are explanatory diagrams of dose information maps of a fluorescent agent (phosphor) in the dose control apparatus shown in FIG. 13.
Figure 15B:
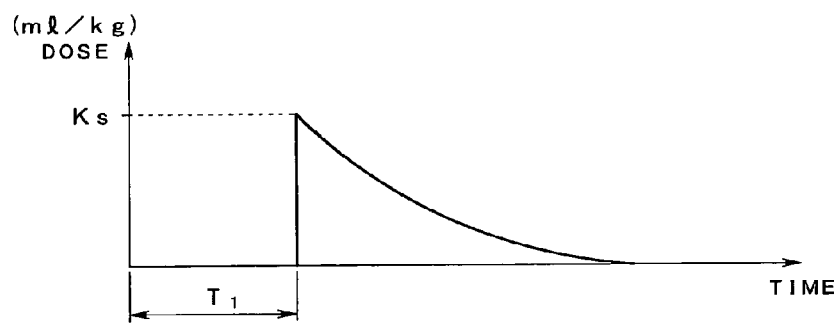

In the dose data memory portion 121*b*, a required dose determined beforehand by an experiment, theoretical calculation, and the like is stored as a map in correspondence to the time (dose information map). In this dose information map, for example, the dose Ks is set in such a way as to decrease continuously and linearly with the passage of time after the administration start time T1, as shown in FIG. 15A. The dose information map may have a nonlinear characteristic as shown in FIG. 15B. This characteristic is essentially determined by an experiment, theoretical calculation, and the like. The dose information map stored in the dose data memory portion 121*b* is read by the dose data correction portion 121*d*, as needed.

Figure 15C:
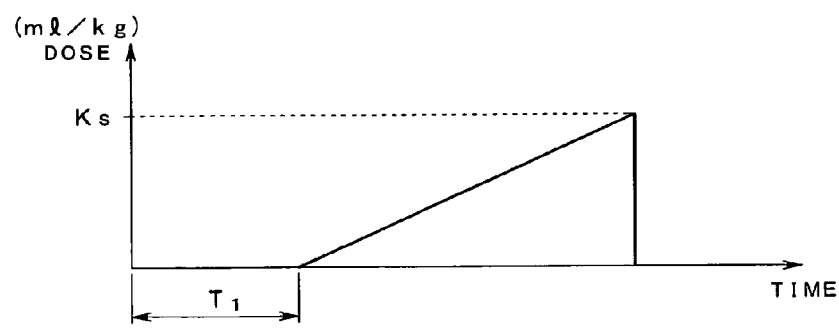
Figure 15D:
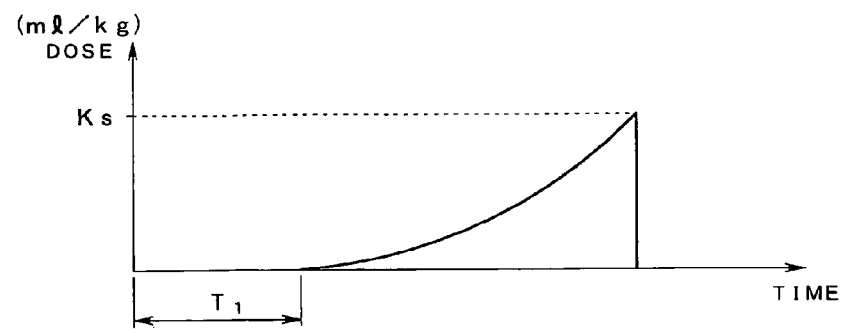

The dose information map is not limited to the above-described form. For example, the dose may not be decreased continuously with the passage of time, but a constant dose may be administered continuously or the dose may be fluctuated continuously with the passage of time. The dose may not be decreased with the passage of time as shown in FIG. 15A, but the dose may be set to increase continuously and linearly with the passage of time after the administration start time T1 as shown in FIG. 15C, for example. Likewise, for FIG. 15B, the dose may not be decreased with the passage of time, but the dose may be set to increase continuously with the passage of time after the administration start time T1 while a nonlinear characteristic is exhibited as shown in FIG. 15D, for example.

The general living body function information, e.g., a heart rate, on a weight, age, sex, and the like basis is stored as living body information reference values in the living body information reference value memory portion 121c. These living body information reference values are read by the dose data correction portion 121d, as needed.

When the automatic administration apparatus 120 is in operation, the living body function information of the inspection object 101 is always input from the living body information detection portion 200 into the dose data correction portion 121d. The dose data correction portion 121d compares the input living body function information with the living body function information reference value stored in the living body information reference value memory portion 121c, and judges whether the dose and the administration time are appropriate or not. When it is judged as being not appropriate, the dose data correction portion 121d corrects at least one of the dose and the administration time. For example, correction is conducted in such a way that the administration time is increased when the heart rate is increased, the administration time is decreased when the heart rate is decreased, and the like. The correction signals of the dose and the administration time are transmitted from the dose data correction portion 121d to the automatic administration apparatus 120. The automatic administration apparatus 120 adjusts the administration of the fluorescent agent (phosphor), based on the correction signals. A series of these processes is conducted a predetermined times within the time of administration of the fluorescent agent (phosphor).

The administration finishing condition judgment portion 121e judges whether the administration finishing condition has been input by the operator and whether this administration finishing condition has been satisfied or not, and outputs a signal to the main control portion 121f when the condition has been satisfied. Here, the administration finishing condition refers to, for example, a total time of automatic administration of the fluorescent agent (phosphor), a total dose of the fluorescent agent (phosphor), intentional OFF of the automatic administration (switching operation by the operator), and the like. When any one of these conditions has been satisfied, a signal for finishing the administration is output to the main control portion 121f.

The automatic administration start time T1 is input into the main control portion 121f by the operator. After the main control portion 121f judges that the automatic administration start time T1 is reached, the main control portion 121f sets the dose of the fluorescent agent (phosphor) in correspondence to the time based on the dose information map of the dose data memory portion 121b.

When the automatic administration apparatus 120 is in operation (when the automatic administration apparatus 120 is ON), the main control portion 121f outputs a signal in correspondence to the dose to the automatic administration apparatus 120, and allows the monitor portion 121g to display the dose and the administration time. On the other hand, when the automatic administration apparatus 120 is not in operation (when the automatic administration apparatus 120 is OFF), the main control portion 121f allows the monitor portion 121g to display an indication that the automatic administration apparatus 120 is OFF and display the dose and the administration time. When a signal for finishing the administration is input from the administration finishing condition judgment portion 121e, the automatic administration is allowed to finish.

In the case where the fluorescent agent (phosphor) is administered again into the living body after the automatic administration is finished, the main control portion 121f judges the start time of readministration based on the peak time of the concentration of the fluorescent agent (phosphor) in the living body, the peak time being input from the fluorescent agent concentration measuring apparatus 1. That is, the main control portion 121f sets the start time of readministration at a predetermined time before or after the peak time of the concentration of the fluorescent agent (phosphor) in the living body, the peak time being estimated by the fluorescent agent concentration measuring apparatus 1. It is preferable that the start time of readministration is set based on the time difference between the administration start time of the last administration and the estimated peak time of the concentration in the living body, although not limited to this. When the main control portion 121f judges that the set start time of readministration is reached, the main control portion 121f sets the dose of the fluorescent agent (phosphor) in correspondence to the time, as described above. In this manner, the dose control apparatus 121 can control in such a way that the concentration of the fluorescent agent (phosphor) in the living body reaches again its peak a predetermined time after the peak time of the concentration in the living body.

As described above, the dose control apparatus 121 is configured to include the functions of an administration start judgment portion, a dose setting portion, and an output portion.

The dose control program executed by the dose control apparatus 121 will be described below with reference to the flow chart shown in FIG. 16.

In step S101, the automatic administration start time T1 input by the operator is read. Subsequently, step S102 is executed, wherein it is judged whether the automatic administration start time T1 is reached or not.

When it is judged in step S102 that the automatic administration start time T1 is reached, step S103 is executed, wherein the dose is set based on the time from the start of the automatic administration with reference to the predetermined map (dose information map).

Thereafter, step S104 is executed, wherein it is judged whether the automatic administration apparatus 120 is ON or not. When the result of this judgment is ON, step S105 is executed, wherein the living body information detection portion 200 detects the living body function information of the inspection object 101 and transmits the living body function information to the dose data correction portion 121d.

Step S106 is executed, wherein the dose data correction portion 121d judges whether the dose of the fluorescent agent (phosphor) is appropriate or not, based on the living body function information. When it is appropriate as a result, step S107 is executed, wherein the signal in correspondence to the dose set in step S103 is output to the automatic administration apparatus 120, and step S110 is executed. Conversely, when it is not appropriate, step S108 is executed, wherein the dose data correction portion 121d corrects at least one of the dose and the administration time and outputs the signal in correspondence to the corrected dose or administration time, and step S110 is executed.

On the other hand, when the automatic administration apparatus 120 is OFF in the above-described step S104, step 109 is executed, wherein the monitor portion 121g is allowed to display that the automatic administration apparatus is OFF, and step S110 is executed.

When step S110 is executed after step S107, step S108, or step S109, the monitor portion 121g is allowed to display the dose and the administration time. In the case where the dose and the administration time are displayed on the monitor portion 121g during the automatic administration apparatus 120 is OFF, the operator administers the fluorescent agent (phosphor) by oneself.

Step S111 is executed, wherein it is judged whether the administration finishing condition is established or not. When the administration finishing condition is not established, the processing from step S103 is repeated. When the administration finishing condition is established, step S112 is executed. Each data (clocked time and the like) is cleared, and step S113 is executed. The monitor portion 121g is allowed to display finish of the administration, and the program is finished.

That is, in the previously known case, as indicated by a broken line shown in FIG. 17, a peak of fluorescence intensity is exhibited a predetermined time Tp after the initial administration, and after that, the fluorescence intensity is decreased gradually since the fluorescent agent (phosphor) is metabolized. However, in the case where the fluorescent agent (phosphor) is administered by using the dose control apparatus 121 according to the present third embodiment, as indicated by a solid line shown in FIG. 17, the fluorescence intensity close to peak can be maintained for a while after the peak is reached.

Consequently, even in the state in which the fluorescence intensity precisely at the peak is not attained due to, for example, the individual difference of the inspection object 101, a favorable fluorescence observation can be conducted nearly at the peak with flexibility.

Since the state in which the fluorescence intensity is close to the peak can be maintained for a long time, there is no need to precisely grasp the time at which the fluorescence intensity reaches its peak, so that leeway can be given to the observation and the observation can be conducted stably.

There is no need to conduct a plurality of times of observation aiming at the peak of the fluorescence intensity and, therefore, an observation can be conducted while very small load is applied to the observer and the inspection object 101.

When the automatic administration apparatus 120 is in operation, the dose data correction portion 121d can correct repeatedly the dose and the administration time of the fluorescent agent (phosphor), based on the living body function information of the inspection object 101. As a result, an optimum dose of fluorescent agent (phosphor) can be administered from the automatic administration apparatus 120 to the inspection object 101 in correspondence to the variations in the metabolism of the inspection object 101 with time.

The dose control apparatus 121 can control in such a way that the concentration of the fluorescent agent in the living body reaches again its peak after the readministration time, based on the peak time of the concentration of the fluorescent agent (phosphor) in the living body estimated by the fluorescent agent concentration measuring apparatus 1. Here, the state in which the fluorescence intensity is close to the peak can be maintained for a longer time by the readministration of the fluorescent agent at a predetermined time before the estimated peak time of the concentration in the living body.

Fourth Embodiment

Figure 18:
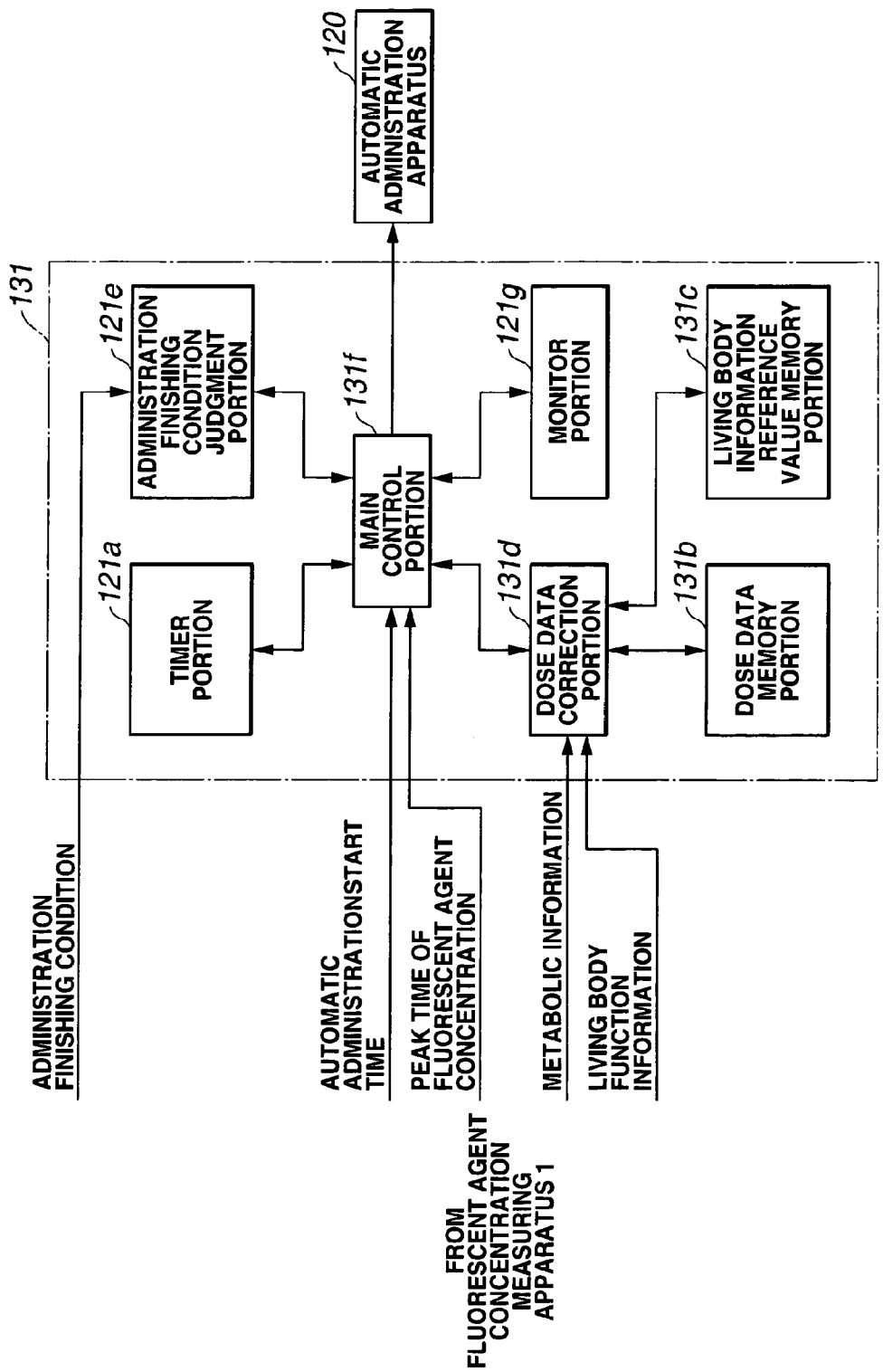
FIG. 18 is a functional block diagram of a dose control apparatus according to a fourth embodiment of the present invention.
Figure 19:
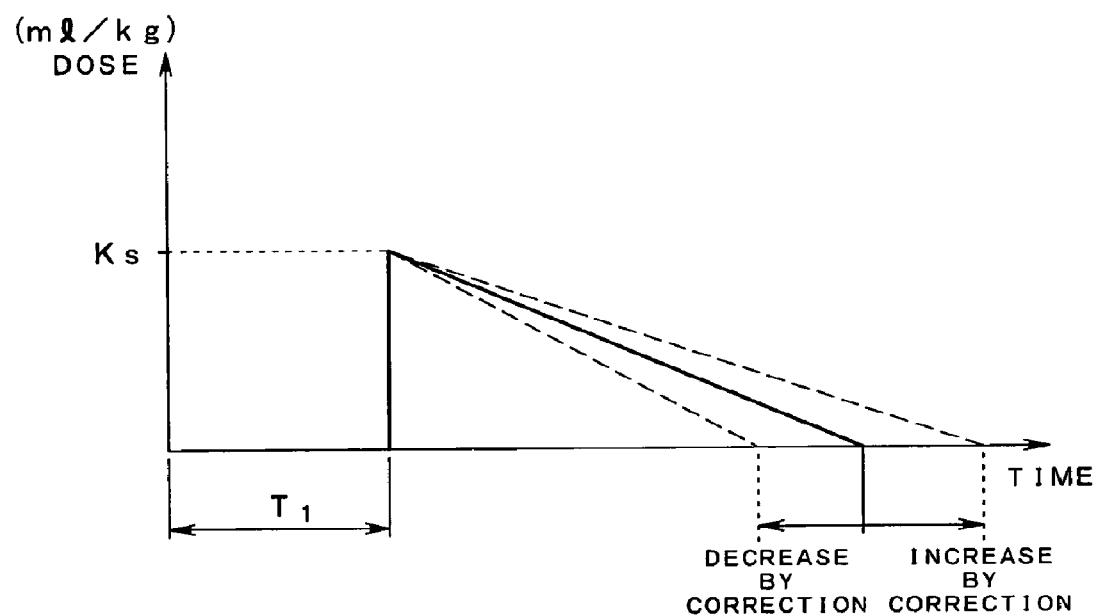
FIG. 19 is an explanatory diagram of the correction of dose information map of the fluorescent agent in the dose control apparatus shown in FIG. 18.
Figure 20:
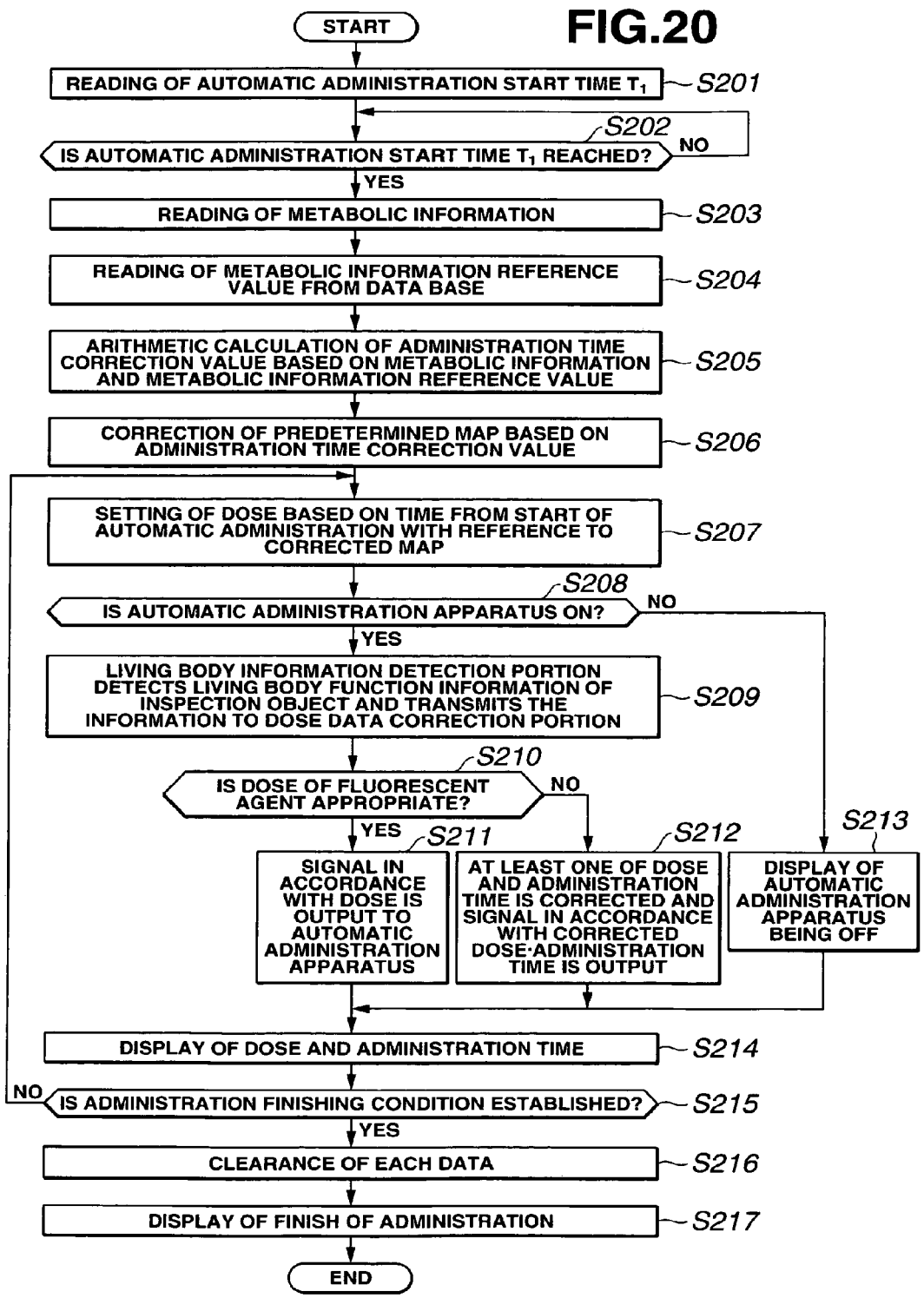
FIG. 20 is a flow chart of a dose control program in the dose control apparatus shown in FIG. 18.

FIG. 18 to FIG. 20 show a fourth embodiment of the present invention. FIG. 18 is a functional block diagram of a dose control apparatus. FIG. 19 is an explanatory diagram of the correction of dose information map of the fluorescent agent (phosphor). FIG. 20 is a flow chart of a dose control program. The present fourth embodiment is different from the above-described third embodiment in the point that the dose information map in the dose control apparatus is freely corrected in correspondence to the metabolic information, and other configuration and operation are similar to those in the third embodiment. Therefore, the same configurations are indicated by the same reference numerals as those set forth above and explanations thereof will not be provided.

That is, as shown in FIG. 18, for a dose control apparatus 131, the automatic administration start time, the administration finishing condition, the metabolic information (described below), and the like are input by an operator, the living body function information is input by the living body information detection portion 200, and the dose and the like in correspondence to the administration time is set based on a dose information map, which is set after correction based on the metabolic information, while following the dose control program described below. When the administration time is reached, the dose control apparatus 131 outputs an output signal in correspondence to the dose to the automatic administration apparatus 120 (in the case where automatic administration is conducted by the automatic administration apparatus 120) and, in addition, the dose, the administration time, and the like are displayed on the monitor portion 121g.

The dose control apparatus 131 corrects the dose or the administration timing of the fluorescent agent (phosphor) when the living body function information of the inspection object 101 detected by the living body information detection portion 200 varies during the automatic administration by the automatic administration apparatus 120.

Here, the above-described metabolic information is attained beforehand from the inspection object 101 through, for example, an inspection of the concentration in the blood. For example, the information is attained from the concentration of an enzyme, e.g., γ-GTP (γ-glutamyltranspeptidase) and GOT (glutamic-oxaloacetic transaminase), in the blood or an enzyme, e.g., cathepsin B, cathepsin L, or uPA (urokinase-type plasminogen activator), observed when a cancer occurs.

In order to realize the above-described dose control function, the dose control apparatus 131 is primarily configured to include, for example, a timer portion 121a, an administration finishing condition judgment portion 121e, a monitor portion 121g, a dose data memory portion 131b, a living body information reference value memory portion 131c, a dose data correction portion 131d, and a main control portion 131f, as shown in FIG. 18.

In the dose data memory portion 131b, a required dose, which is determined beforehand by an experiment, theoretical calculation, and the like and is in correspondence to the above-described metabolic information reference value and living body function information reference value, is stored as a map in correspondence to the time (dose information map). In this dose information map, for example, the dose Ks is set in such a way as to decrease continuously and linearly with the passage of time after the administration start time T1, as indicated by a solid line shown in FIG. 19. The dose information map stored in the dose data memory portion 131b is read by the dose data correction portion 131d, as needed.

The general metabolic information of the above-described enzyme and the living body function information, e.g., a heart rate, on a weight, age, sex, and the like basis is stored as metabolic information reference values and living body function information reference values, respectively, in the living body information reference value memory portion 131c. These metabolic information reference values and living body function information reference values are read by the dose data correction portion 131d, as needed.

The metabolic information of the inspection object 101 is input by the operator into the dose data correction portion 131d. The living body function information is input from the living body information detection portion 200. The metabolic information reference values and the living body function information reference values are input from the living body information reference value memory portion 131c. The dose information map is input from the dose data memory portion 131b.

The dose data correction portion 131d compares the metabolic information of the inspection object 101 with the metabolic information reference value, and judges the magnitude correlation. For example, when the metabolic information of the inspection object 101 is larger than the metabolic information reference value by 10%, the administration time of the fluorescent agent (phosphor) is corrected so as to increase by 10%. Conversely, when the metabolic information of the inspection object 101 is smaller than the metabolic information reference value by 10%, the administration time of the fluorescent agent (phosphor) is corrected so as to decrease by 10%. An example of this correction is indicated by broken lines shown in FIG. 19. The example of the correction shown here is no more than one example, and there may be other examples of the correction (for example, the proportion of the time increased by the correction is differentiated from that of the time decreased by the correction). The dose may be increased with the passage of time in contrast to that shown in FIG. 19, wherein the dose is decreased, and the correction may be conducted by the dose data correction portion 131d in such a way that the increasing rate is changed. Furthermore, the above-described correction methods may be combined, so that the dose is changed and the finish time is changed correspondingly, or the correction may be conducted by the dose data correction portion 131d in such a way that the increasing rate is changed.

When the automatic administration apparatus 120 is in operation, the living body function information of the inspection object 101 is always input from the living body information detection portion 200 into the dose data correction portion 131d. The dose data correction portion 131d compares the input living body function information with the living body function information reference value stored in the living body information reference value memory portion 131c, and judges whether the dose and the administration time are appropriate or not. When it is judged as being not appropriate, the dose data correction portion 131d corrects at least one of the dose and the administration time. For example, correction is conducted in such a way that the administration time is increased when the heart rate is increased, the administration time is decreased when the heart rate is decreased, and the like. The correction signals of the dose and the administration time are transmitted from the dose data correction portion 131d to the automatic administration apparatus 120. The automatic administration apparatus 120 adjusts the administration of the fluorescent agent (phosphor), based on the correction signals. A series of these processes is conducted a predetermined times within the time of administration of the fluorescent agent (phosphor).

The automatic administration start time T1 is input into the main control portion 131f by the operator. After the main control portion 131f judges that the automatic administration start time T1 is reached, the main control portion 131f sets the dose of the fluorescent agent (phosphor) in correspondence to the time based on the dose information map corrected by the dose data correction portion 131d. When the automatic administration apparatus 120 is in operation (when the automatic administration apparatus 120 is ON), the main control portion 131f outputs a signal in correspondence to the dose to the automatic administration apparatus 120, and allows the monitor portion 121g to display the dose and the administration time. On the other hand, when the automatic administration apparatus 120 is not in operation (when the automatic administration apparatus 120 is OFF), the main control portion 131f allows the monitor portion 121g to display an indication that the automatic administration apparatus 120 is OFF and display the dose and the administration time. When a signal for finishing the administration is input from the administration finishing condition judgment portion 121e, the automatic administration is allowed to finish.

In the case where the fluorescent agent (phosphor) is administered again into the living body after the automatic administration is finished, as in the third embodiment, the main control portion 131f judges the start time of readministration, based on the peak time of the concentration of the fluorescent agent in the living body, the peak time being input from the fluorescent agent concentration measuring apparatus 1. When the main control portion 131f judges that the set start time of administration is reached, the main control portion 131f sets the dose of the fluorescent agent in correspondence to the time. In this manner, the dose control apparatus 131 can control in such a way that the concentration of the fluorescent agent in the living body reaches again its peak a predetermined time after the peak time of the concentration in the living body.

As described above, the dose control apparatus 131 is configured to include the functions of an administration start judgment portion, a dose setting portion, and an output portion.

The dose control program executed by the dose control apparatus 131 will be described below with reference to the flow chart shown in FIG. 20. In step S201, the automatic administration start time T1 input by the operator is read. Subsequently, step S202 is executed, wherein it is judged whether the automatic administration start time T1 is reached or not.

When it is judged that the automatic administration start time T1 is reached in step S202, step S203 is executed, wherein the metabolic information is read.

Step S204 is executed, wherein the metabolic information reference value is read from the data base (the dose data memory portion 131b).

Step S205 is executed. The metabolic information read in step S203 is compared with the metabolic information reference value read in step S204, and the correction value of the administration time, that is, the degree of increase by the correction or the degree of decrease by the correction, is arithmetically calculated.

Step S206 is executed, wherein the predetermined map (dose information map) is corrected based on the correction value arithmetically calculated in step S205.

Step S207 is executed, wherein the dose is set based on the time from the start of the automatic administration with reference to the dose information map corrected in step S206.

Thereafter, step S208 is executed, wherein it is judged whether the automatic administration apparatus 120 is ON or not. When the result of this judgment is ON, step S209 is executed, wherein the living body information detection portion 200 detects the living body function information of the inspection object 101 and transmits the living body function information to the dose data correction portion 131d.

Step S210 is executed, wherein the dose data correction portion 131d judges whether the dose of the fluorescent agent (phosphor) is appropriate or not based on the living body function information. When it is appropriate as a result, step S211 is executed, wherein the signal in correspondence to the dose set in step S207 is output to the automatic administration apparatus 120, and step S214 is executed. Conversely, when it is not appropriate, step S212 is executed, wherein the dose data correction portion 131d corrects at least one of the dose and the administration time and output the signal in correspondence to the corrected dose or administration time, and step S214 is executed.

On the other hand, when the automatic administration apparatus 120 is OFF in the above-described step S208, step 213 is executed, wherein the monitor portion 121g is allowed to display that the automatic administration apparatus is OFF, and step S214 is executed.

When step S214 is executed after step S211, step S212, or step S213, the monitor portion 121g is allowed to display the dose and the administration time. In the case where the dose and the administration time are displayed on the monitor portion 121g during the automatic administration apparatus 120 is OFF, the operator administers the fluorescent agent (phosphor) by oneself.

Step S215 is executed, wherein it is judged whether the administration finishing condition is established or not. When the administration finishing condition is not established, the processing from step S207 is repeated. When the administration finishing condition is established, step S216 is executed. Each data (clocked time and the like) is cleared, and step S217 is executed. The monitor portion 121g is allowed to display finish of the administration, and the program is finished.

As described above, according to the present fourth embodiment, the effects described for the above-described third embodiment can be exerted, as a matter of course. Furthermore, since the dose information map is set after being corrected based on the metabolic information, the peak of the fluorescence intensity can be stably and precisely maintained for a long time without being influenced by the individual difference of the inspection object 101 and the variations with time of the metabolism, so that the fluorescence observation can easily be conducted.

Fifth Embodiment

Figure 21:
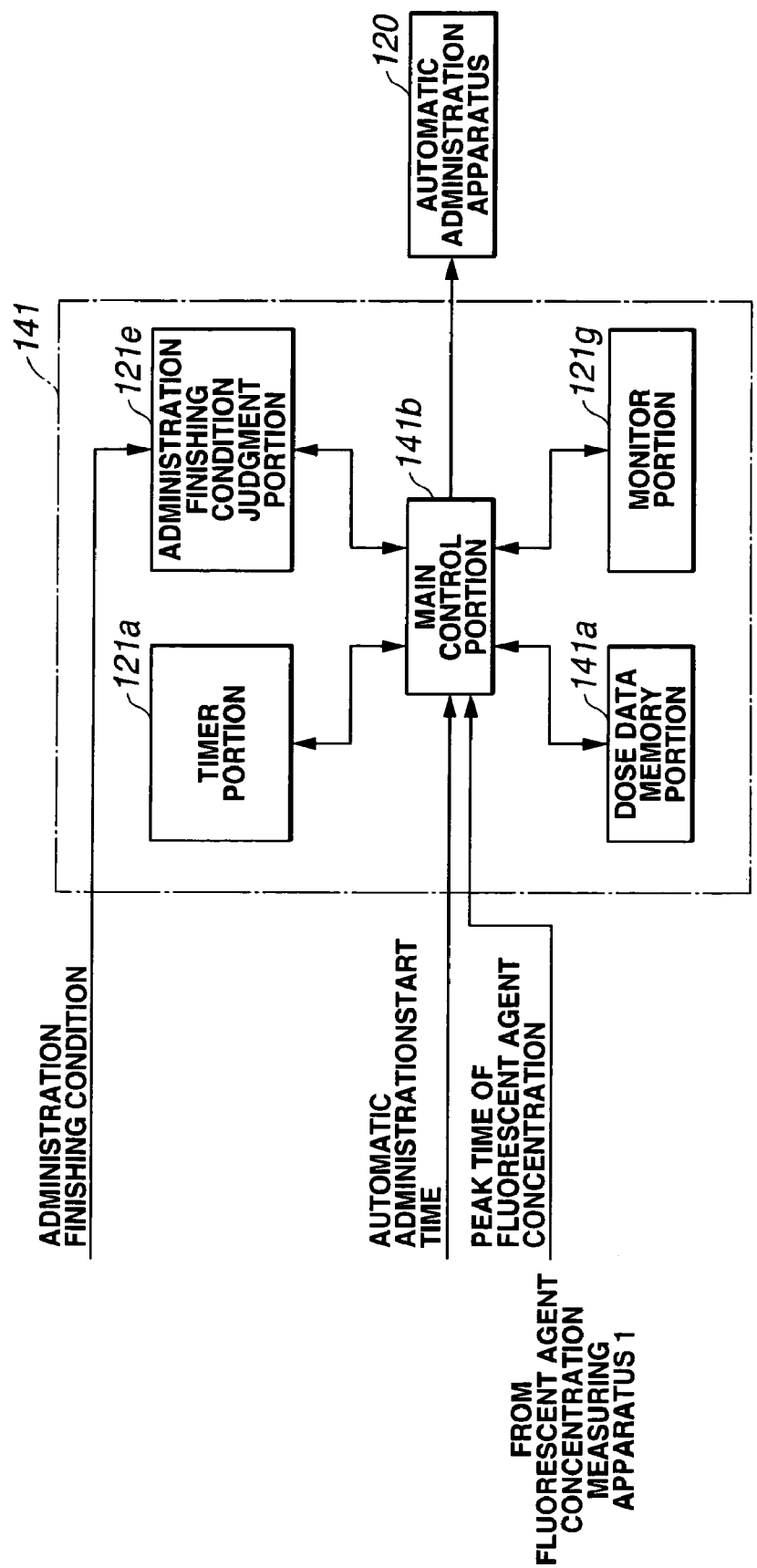
FIG. 21 is a functional block diagram of a dose control apparatus according to a fifth embodiment of the present invention.
Figure 22:
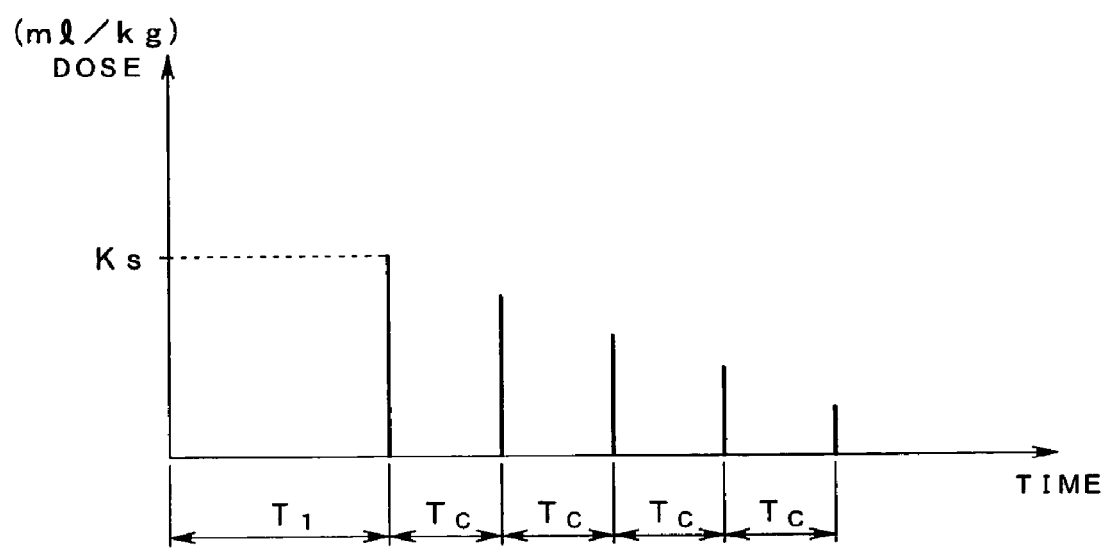
FIG. 22 is an explanatory diagram of a dose information table of a fluorescent agent in the dose control apparatus shown in FIG. 21.
Figure 23:
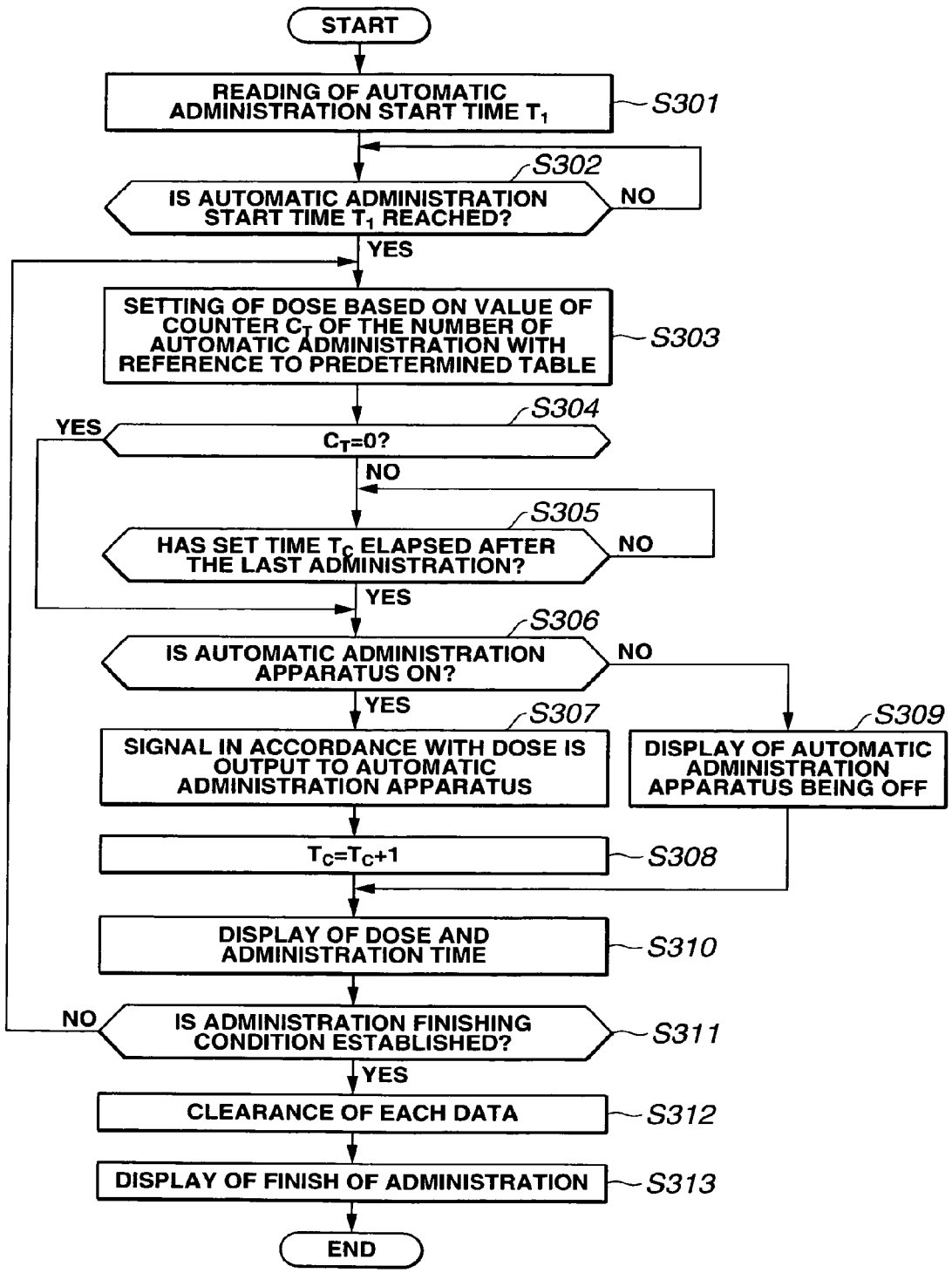
FIG. 23 is a flow chart of a dose control program in the dose control apparatus shown in FIG. 21.

FIG. 21 to FIG. 23 show a fifth embodiment of the present invention. FIG. 21 is a functional block diagram of a dose control apparatus. FIG. 22 is an explanatory diagram of a dose information table of a fluorescent agent (phosphor). FIG. 23 is a flow chart of a dose control program. The present fifth embodiment is different from the above-described first embodiment in the point that the administration of a fluorescent agent (phosphor) by the dose control apparatus is conducted at a predetermined time interval, and other configuration and operation are similar to those in the above-described first embodiment. Therefore, the same configurations are indicated by the same reference numerals as those set forth above and explanations thereof will not be provided.

That is, in FIG. 21, reference numeral 141 denotes a dose control apparatus according to the present fifth embodiment, and an automatic administration start time, an administration finishing condition, and the like are input into this dose control apparatus 141 by the operator. The dose control apparatus 141 sets the dose and the like on a predetermined time interval basis (on the number of administration basis) based on the dose information table, (in the case where automatic administration is conducted by the automatic administration apparatus 120) outputs an output signal in correspondence to the dose to the automatic administration apparatus 120 when the administration is conducted and, in addition, display the dose, the administration time, and the like on the monitor portion 121g, while following the dose control program.

In order to realize the above-described dose control function, the dose control apparatus 141 is primarily configured to include, for example, a timer portion 121a, an administration finishing condition judgment portion 121e, a monitor portion 121g, a dose data memory portion 141a, and a main control portion 141b, as shown in FIG. 21.

In the dose data memory portion 141a, a required dose, which is determined beforehand by an experiment, theoretical calculation, and the like is stored as a table (dose information table) on a time interval basis (on the number of administration basis). In this dose information table, for example, the dose is set in such a way as to decrease with an increase in the number of administration after the administration start time T1, as shown in FIG. 22. The dose information table stored in the dose data memory portion 141a is read by the main control portion 141b, as needed.

The automatic administration start time T1 is input into the main control portion 141b by the operator. After the main control portion 141b judges that the automatic administration start time T1 is reached, the main control portion 141b sets the dose of the fluorescent agent (phosphor) on a predetermined time interval basis (on the number of administration basis) based on the dose information table stored in the dose data memory portion 141a. When the automatic administration apparatus 120 is in operation (when the automatic administration apparatus 120 is ON), the main control portion 141b outputs a signal in correspondence to the dose to the automatic administration apparatus 120, and allows the monitor portion 121g to display the dose and the administration time. On the other hand, when the automatic administration apparatus 120 is not in operation (when the automatic administration apparatus 120 is OFF), the main control portion 141b allows the monitor portion 121g to display an indication that the automatic administration apparatus 120 is OFF and display the dose and the administration time. When a signal for finishing the administration is input from the administration finishing condition judgment portion 121e, the automatic administration is allowed to finish.

In the case where the fluorescent agent (phosphor) is administered again into the living body after the automatic administration is finished, as in the third embodiment, the main control portion 141b judges the start time of readministration, based on the peak time of the concentration of the fluorescent agent in the living body, the peak time being input from the fluorescent agent concentration measuring apparatus 1. When the main control portion 141b judges that the set start time of administration is reached, the main control portion 141b sets the dose of the fluorescent agent in correspondence to the time. In this manner, the dose control apparatus 141 can control in such a way that the concentration of the fluorescent agent in the living body reaches again its peak a predetermined time after the peak time of the concentration in the living body.

As described above, the dose control apparatus 141 is configured to include the functions of an administration start judgment portion, a dose setting portion, and an output portion. A dose information table, in which the dose is increased or fluctuated on a time interval basis in contrast to that shown in FIG. 22 where the dose is decreased, may be stored in the dose data memory portion 141a and the table may be read by the main control portion 141b.

The dose control program executed by the dose control apparatus 141 will be described below with reference to the flow chart shown in FIG. 23. In step S301, the automatic administration start time T1 input by the operator is read. Subsequently, step S302 is executed, wherein it is judged whether the automatic administration start time T1 is reached or not.

When it is judged in step S302 that the automatic administration start time T1 is reached, step S303 is executed, wherein the dose is set based on a value of a counter CT of the number of automatic administration with reference to the predetermined table (dose information table). The counter CT of the number of automatic administration is a counter to count the number of administration, and an initial value is set at 0.

Subsequently, step S304 is executed, wherein it is judged whether the counter CT of the number of automatic administration is 0 (initial time) or not. When the counter CT of the number of automatic administration is 0 (initial time), step S306 is executed successively to conduct the administration of the fluorescent agent (phosphor).

When the counter CT of the number of automatic administration is not 0 (initial time), step S305 is executed. It is judged whether the set time Tc has elapsed after the last administration. When the set time Tc has elapsed, step S306 is executed to conduct the administration of the fluorescent agent (phosphor).

When step S306 is executed to conduct the administration of the fluorescent agent (phosphor), it is judged whether the automatic administration apparatus 120 is ON or not. In the case of ON, step S307 is executed, wherein a signal in correspondence to the dose set in step S303 is output to the automatic administration apparatus 120. Subsequently, step S308 is executed, wherein the counter CT of the number of automatic administration is incremented (CT=CT+1) for the next administration, and step S310 is executed.

Conversely, when the automatic administration apparatus 120 is OFF, step S309 is executed, wherein the monitor portion 121g is allowed to display that the automatic administration apparatus is OFF, and step S310 is executed.

When step S310 is executed after step S308 or step S309, the monitor portion 121g is allowed to display the dose and the administration time. In the case where the dose and the administration time are displayed on the monitor portion 121g during the automatic administration apparatus 120 is OFF, the operator administers the fluorescent agent (phosphor) by oneself.

Step S311 is executed, wherein it is judged whether the administration finishing condition is established or not. When the administration finishing condition is not established, the processing from step S303 is repeated. When the administration finishing condition is established, step S312 is executed. Each data (clocked time, the counter CT of the number of automatic administration, and the like) is cleared, and step S313 is executed. The monitor portion 121g is allowed to display finish of the administration, and the program is finished.

As described above, the effects as in the above-described third embodiment can be exerted by administering the fluorescent agent (phosphor) at a predetermined time interval as in the fifth embodiment.

In the above-described third to fifth embodiments, the fluorescent drug (fluorescent agent, phosphor) is administered intravenously, although not limited to this. The administration may be conducted to the inspection object 101 orally or by spraying in the body. For the oral administration, the monitor portion 121g displays the administration timing for the oral administration of the fluorescent agent. The inspection object 101 takes a predetermined dose of fluorescent drug according to the displayed administration timing. For the spraying in the body, a drip infusion tube 125 is inserted into an endo-therapy product insertion channel (not shown in the drawing) disposed in the inside of the endoscope 105 of the fluorescence endoscope system 102 serving as an internal medical device. According to this configuration, the fluorescent agent dripped from the drip infusion container 119 of the automatic administration apparatus 120 is sprayed into the living body lumen 101a of the inspection object 101 from the vicinity of the distal end of the endoscope 105 through the drip infusion tube 125.

In the explanation of each of the above-described embodiments, the fluorescent agent (phosphor), e.g., a solution, in which an indocyanine green derived labeled antibody is dissolved, is taken as an example. However, it is a matter of course that the present invention can be applied to other fluorescent agents.

The present invention is not limited to the above-described embodiments, and various modifications and rearrangements can be made within the scope of the gist of the present invention.

What is claimed is:

1. A fluorescent agent concentration measuring apparatus comprising:
    an excitation light source to radiate excitation light to a sample containing a body fluid taken from a living body administered with a fluorescent drug, the excitation light allowing the drug to emit fluorescence;
    a fluorescence detection portion to detect the fluorescence;
    a fluorescent agent concentration calculation portion to calculate the concentration of the drug in the living body, based on a detection signal from the fluorescence detection portion;
    a curve data storage portion to pre-store, as a pattern, curve data that indicates a relation of concentrations of the drug in the living body at a plurality of times of day; and
    a peak time estimation portion configured to compare the elapsed time after administration of the drug to the living body and the calculated concentration of the drug with the pattern pre-stored in the curve data storage portion and configured to estimate the elapsed time after administration the concentration of the drug in the living body is at a peak.

2. The fluorescent agent concentration measuring apparatus according to claim 1, further comprising a container loading portion to removably dispose a container including the sample solution on an optical path of the excitation light.

3. The fluorescent agent concentration measuring apparatus according to claim 2, further comprising a light shield portion to shield the container loaded in the container loading portion from the external light.

4. The fluorescent agent concentration measuring apparatus according to claim 1, wherein, in a optical path from the excitation light source to the fluorescence detection portion, one or more optical members and one or more optical filters are disposed, wherein each of the one or more optical members and each of the one or more optical filters have a predetermined refraction index constant in a plane orthogonal to an optical axis of the optical path.

5. The fluorescent agent concentration measuring apparatus according to claim 4, wherein each of the one or more optical members has a different predetermined refraction index.

6. The fluorescent agent concentration measuring apparatus according to claim 4, wherein each of the one or more optical filters has a different predetermined refraction index.

7. The fluorescent agent concentration measuring apparatus according to claim 1, wherein the excitation light source is configured to include a single wavelength.

* * * * *